(12) United States Patent
Jardet et al.

(10) Patent No.: US 12,071,648 B2
(45) Date of Patent: Aug. 27, 2024

(54) EX VIVO MODEL OF INFLAMED HUMAN SKIN AND USES THEREOF FOR SCREENING ANTI-INFLAMMATORY COMPOUNDS

(71) Applicant: GENOSKIN, Toulouse (FR)

(72) Inventors: Claire Jardet, Cugnaux (FR); Pascal Descargues, Toulouse (FR); Hanne Norsgaard, Nordhavn (DK); Paola Lovato, København (DK)

(73) Assignee: GENOSKIN, Toulouse (FR)

( * ) Notice: Subject to any disclaimer, the term of this patent is extended or adjusted under 35 U.S.C. 154(b) by 619 days.

(21) Appl. No.: 16/650,492

(22) PCT Filed: Sep. 25, 2018

(86) PCT No.: PCT/EP2018/000448
§ 371 (c)(1),
(2) Date: Mar. 25, 2020

(87) PCT Pub. No.: WO2019/063122
PCT Pub. Date: Apr. 4, 2019

(65) Prior Publication Data
US 2020/0347429 A1 Nov. 5, 2020

(30) Foreign Application Priority Data
Sep. 26, 2017 (FR) .................... 17/71020

(51) Int. Cl.
*C12Q 1/02* (2006.01)
*C12N 5/071* (2010.01)

(52) U.S. Cl.
CPC .......... *C12Q 1/025* (2013.01); *C12N 5/0629* (2013.01); *C12N 2501/15* (2013.01); *C12N 2501/2301* (2013.01); *C12N 2501/2302* (2013.01); *C12N 2501/2323* (2013.01); *C12N 2501/51* (2013.01); *C12N 2501/515* (2013.01)

(58) Field of Classification Search
CPC .. C12Q 1/025; C12N 5/0629; C12N 2501/15; C12N 2501/2301; C12N 2501/2302; C12N 2501/2323; C12N 2501/51; C12N 2501/515
See application file for complete search history.

(56) References Cited

U.S. PATENT DOCUMENTS

2015/0132737 A1* 5/2015 Descargues ............ A01N 1/02

FOREIGN PATENT DOCUMENTS

| EP | 2019316 A2 | 1/2009 | |
|---|---|---|---|
| WO | WO2014083099 | * 6/2014 | ............ A61K 45/06 |
| WO | 2014/182655 A1 | 11/2014 | |

OTHER PUBLICATIONS

Boniface et al., A role for T cell-derived interleukin 22 in psoriatic skin inflammation, Clinical and Experimental Immunology, 150: 407-415. (Year: 2007).*
Ma et al., IL-22 is required for Th17 cell-mediated pathology in a mouse model of psoriasis-like skin inflammation, 118(2): 597-607. (Year: 2008).*
Sakata et al., Prostaglandin E receptor subtypes EP2 and EP4 promote Th1 cell differentiation and Th17 cell expansion through different signaling modules, 58: S244-S248. (Year: 2009).*
Hashizume et al., In vitro propagation and dynamics of T cells from skin biopsies by methods using interleukins-2 and -4 and anti-CD3/CD28 antibody-coated microbeads, Acta Dermato-Venereologica, 90: 468-473. (Year: 2010).*
Mailer et al., IL-1beta promotes Th17 differentiation by inducing alternative splicing of FOXP3, Nature Scientific Reports, p. 1-9. (Year: 2015).*
Fujiyama et al., Topical application of vitamin D3 analogue and corticosteroid to psoriasis plaques decreases skin infiltration of Th17 cells and their ex vivo expansion, Journal of Allergy and Clinical Immunology, 138(2): 517-528.e5 (Year: 2016).*
International Search Report, dated Nov. 14, 2018, from corresponding PCT application No. PCT/EP2018/000448.
Bogaard et al.; Crosstalk between Keratinocytes and T Cells in a 3D Microenvironment: A Model to Study Inflammatory Skin Diseases; Journal of Investigative Dermatology; Mar. 1, 2014; pp. 719-727; vol. 134, No. 3.
Koenen et al.; Human CD25highFoxp3pos regulatory T cells differentiate into IL-17-producing cells; Blood; Sep. 15, 2008; pp. 2340-2352; vol. 112, No. 6.
Desmet et al.; In vitro psoriasis models with focus on reconstructed skin models as promising tools in psoriasis research; Experimental Biology and Medicine; Jun. 1, 2017; pp. 1158-1169; vol. 242, No. 11.
Tjabringa et al.; Development and Validation of Human Psoriatic Skin quivalents; The American Journal of Pathology; Sep. 1, 2008; pp. 815-823; vol. 173, No. 3.
Calapre et al.; Heat-mediated reduction of apoptosis in UVB-damaged keratinocytes in vitro and in human skin ex vivo; BMC Dermatology; May 26, 2016; vol. 16, No. 1.

* cited by examiner

*Primary Examiner* — Laura Schuberg
*Assistant Examiner* — Joseph Paul Miano
(74) *Attorney, Agent, or Firm* — NIXON & VANDERHYE

(57) ABSTRACT

Disclosed is an ex-vivo model of inflamed skin, an in-vitro method for obtaining the same and uses thereof for screening anti-inflammatory compounds. The method includes injecting, into the dermis of a healthy skin biopsy previously taken from a mammal, a composition including an effective amount for activating dermal resident T cells of an anti-CD3 antibody and an anti-CD28 antibody; and b) incubating the injected skin biopsy obtained in step a) in the presence of a composition including an effective amount, for obtaining the polarization of the T cells activated in step a) into LTh1 and/or LTh17 and the synthesis of inflammation markers, of at least one mixture of IL-1β, IL-23, and TGF-β.

16 Claims, 9 Drawing Sheets

EX VIVO MODEL OF INFLAMED HUMAN SKIN AND USES THEREOF FOR SCREENING ANTI-INFLAMMATORY COMPOUNDS

This patent application claims the priority of French patent application No. 17/71020 filed on Sep. 26, 2017, which is incorporated herein by reference.

FIELD OF THE INVENTION

The present invention relates to a method for obtaining an ex vivo model of inflamed skin, a kit for implementing this method, as well as the uses of the model of inflamed skin obtained by the method of the invention for identifying compounds having an anti-inflammatory effect, in particular for the treatment of psoriasis.

PRIOR ART

Psoriasis is a chronic inflammatory autoimmune disease, affecting about 2% of the European population, characterized by abnormal differentiation and proliferation of epidermal keratinocytes resulting in the formation of often irritating red plaques and an accumulation of dead skin (the scales), which may be located all over the body (most often on the arms, torso, knees, feet, nails, face, and scalp).

Histological analysis of these psoriatic plaques shows an increase in thickness of the epidermis, incomplete differentiation of keratinocytes and a scalloped appearance of the dermal-epidermal junction, accumulation of polynuclear neutrophils in the epidermis and infiltration of the dermis by mononuclear cells, in particular macrophages and T lymphocytes (TL), as well as significant angiogenesis.

Immunohistochemical studies confirm that the dermis is the site of an infiltrate composed mainly of memory $CD4^+$ T lymphocytes, macrophages, and dendritic cells (DC), whereas $CD8^+$ T lymphocytes predominate in normal (non-inflamed) epidermis.

Psoriasis inflammation is the result of the interaction between epithelial cells (keratinocytes), dendritic cells, and T cells. At the molecular level, these interactions are mediated by a complex network of cytokines that initiate the disease and maintain a vicious circle of reciprocal cell activation, thereby perpetuating the skin lesions and their chronicity (J F NICOLAS, Bull. Acad. Natle. Med, 2014, 198 (1), pp. 17-30). The main cytokines produced in psoriatic skin by inflammatory dendritic cells are IL-12 and IL-23, which play an important role in the differentiation or expansion of T lymphocytes into Th1 (LTh1) or Th17 (LTh2) lineages (PECK and MELLINS, Immunology, 2009, 129, pp. 147-153). LTh1s produce IFNγ, TNFα, and IL-2, while LTh17s are responsible for the synthesis of IL-17A, IL-17F, IL-21, IL-22, and to a lesser extent TNFα. This increased production of cytokines is responsible for the activation of keratinocytes, which in turn leads to a release of antimicrobial peptides, pro-inflammatory mediators (IL-1β, IL-6, IL-17C, TNFα, CXCL8, CXCL9, CXCL10, CXCL11, and CCL20) and psoriasin (S100A7). Studies conducted in 2014 have shown that $CD4^+$ T cells producing IL-22, and $CD8^+$ cells producing IL-17 remain present in previously injured psoriatic skin treated with effective psoriatic therapies. These results are similar to those showing that normal-looking, non-lesional skin grafts from patients with psoriasis lead to the development of psoriatic lesions in immunodeficient mice. All this work demonstrates that resident T cells in the skin persist in clinically resolved psoriatic lesions and produce cytokines known to cause the primary pathology of the disease (Rachael A. CLARCK, Sci Transl Med., 2015, 7(269):269rv1).

The treatment of psoriasis is mainly based on the use of corticosteroids, phosphodiesterase inhibitors, immunosuppressants (cyclosporine, tacrolimus), or UV phototherapy. More recently, antibodies against TNFα (infliximab, adalimumab, etanercept, golimumab), IL-17-A (secukinumab, ixekizumab), IL-12/IL-23 (ustekinumab, guselkumab, tildrakizumab) have been developed to control moderate to severe forms of psoriasis or are in clinical trials (GOODERHAM et al., Skin Therapy Letter, 2015, 20(1), pp. 1-5). Some of these antibodies are administered subcutaneously for several weeks or even several years depending on the severity of the psoriasis. Although the treatments have been shown to be somewhat effective, they have significant side effects and are still unable to cure psoriasis. There is a real need to identify new compounds capable of overcoming these disadvantages. To this end, it is essential to have a model of inflamed skin, especially psoriatic skin.

Mouse models of psoriasis are based on spontaneous mutations ($SCd1^{ab}/SCd1^{ab}$, $Sharpin^{cpdm}/Sharpin^{cpdm}$, $Ttc7^{fsn}/Ttc7^{fsn}$) or an artificial modulation of the expression of genes involved in different signaling pathways, or encoding cytokines or growth factors (M P SCHON, Experimental Dermatology, 2008, 17, pp. 703-712). However, these models do not have all the phenotypic and histological characteristics of psoriasis in humans or have additional characteristics that limit the use of these animal models for screening new compounds. Moreover, the physiological differences between humans and animals do not allow to predict with certainty the immune response in humans, leading to the abandonment of many candidate compounds at the preclinical testing phase.

To circumvent these difficulties, xenotransplants of psoriatic human skin have been performed in nude or SCID mice and have allowed to create models of acute forms of psoriasis. However, because the immune system of the recipient mice is incomplete, it is again difficult to extrapolate the results obtained from these animal models to humans.

In addition, the consideration of animal welfare combined with new regulatory requirements is driving the development of models closer to human physiology. Thus, in vitro models of artificial skin or epidermis have been developed from keratinocyte and/or fibroblast culture on inert polycarbonate matrices (SkinEthic™ RHE, EpiSkin™, EPISKIN, France). However, such models do not contain epidermal appendages, nor the components of the immune system, thereby limiting their use for screening potentially irritating compounds.

To overcome these disadvantages, the first ex-vivo models of human skin were made from human skin samples, by taking dermis and epidermis samples. However, the lifespan of these models does not exceed 7 days. This lifespan could be increased by taking, in addition to the dermis and epidermis, the epidermal appendages and hair follicles (EP 2 019 316 B1). However, these models are not consistent with an inflammatory skin condition.

Psoriatic human skin equivalents have been obtained in vitro either by stimulating healthy dermal fibroblasts or by using fibroblasts from patients with psoriasis (TJABRINGA et al., Am. J. Pathol. 2008, 173, pp. 815-823). Although these 3D models show a thickening of the epidermis and production of inflammatory cytokines (TNFα, IL-1α, IL-6, IL-8, and IL-22) which are characteristic of the pathology, the immune component is still absent.

More recently, the addition of IL-1β directly into the culture medium for several days allowed to induce acute inflammation in human skin explants (EP 2 885 637 B1). However, this model does not account for the chronic inflammation observed in psoriasis.

The addition of T cells from peripheral blood, and activated or differentiated into Th1 or Th17 subpopulations, under the dermis of the models developed by Tjabringa et al. has made it possible to demonstrate the influence exerted by the cytokines produced by these T cells on keratinocytes and the development of inflammation (VAN DEN BOGAARD et al., J. Invest. Dermatol. 2014, 134, pp. 719-727). However, certain characteristics of psoriasis, such as the expression of the Ki67 marker, keratinocyte hyperproliferation, and acanthosis, are still absent from this model. In addition, T cells derived from peripheral blood are distinct from resident T cells in the skin, and in particular from memory resident T ($T_{RM}$) cells in the dermis and epidermis (MUELLER and MACKAY, Nat Rev Immunol., 2016, 16(2), pp. 79-89). Indeed, $T_{RM}$ cells have transcription factors and surface markers distinguishing them from other memory T cells in peripheral blood. Thus, the presence of CD69 on the surface of $T_{RS}$s combined with the under-expression of the S1PR1 (Sphingosin-1-phosphate receptor 1) gene allows them to remain in peripheral tissues such as the skin for several months, thereby preventing them from recirculating into the bloodstream. The presence of $CD8^+$ $T_{RM}$ and $CD4^+$ $T_{RM}$ populations has been widely observed in the epidermis and dermis of healthy human skin; the $CD8^+CD49a^+$ $T_{RM}$ subpopulation is involved in the synthesis of perforin and IFNγ while the $CD8^+CD49a^-$ $T_{RM}$ cells mainly produce IL-17 (HAIJING et al., Autoimmun Rev., 2018, pp. 906-911).

Another approach based on the activation of resident T cells in human skin biopsies was described in the international application published under number WO 2014/182655 A1. However, no protein markers characteristic of psoriasis could be identified in this model. In addition, the removal of subcutaneous adipose tissue results in obtaining skin biopsies no more than 300 μm thick. Such fineness makes their handling very delicate and does not allow subcutaneous injections.

There is therefore a real need to develop new tools, in particular ex vivo models of inflamed human skin. This need especially involves the identification of culture conditions under which ex vivo skin samples, suitable for use in inflammation modeling, can be maintained for a sufficiently long time without inducing significant deviation of the behavior of these samples from the conditions encountered in vivo.

Surprisingly, the inventors have developed an in vitro method that overcomes all these disadvantages.

SUMMARY OF THE INVENTION

The present invention allows to compensate for the above-mentioned disadvantages by providing an ex vivo model of inflamed skin which reflects more precisely and reproducibly the environment of the inflamed skin as observed in vivo in a physiopathological context.

Thus, a first object of the invention relates to an in vitro method for obtaining an ex vivo model of inflamed skin comprising the following steps:
 a) injecting, into the dermis of a healthy skin biopsy previously taken from a mammal, a composition comprising an effective amount for activating dermal resident T cells of an anti-CD3 antibody and an anti-CD28 antibody, and optionally IL-2,
 b) incubating the injected skin biopsy obtained in step a) in the presence of a composition comprising an effective amount, for obtaining the polarization of the T cells activated in step a) into LTh1 and/or LTh17 and the synthesis of inflammation markers, of at least one mixture of IL-1β, IL-23, and TGF-β.

A second object of the present invention relates to an ex vivo model of inflamed skin comprising a dermis, an epidermis and epidermal appendages, and in which activated T cells polarized into LTh1 and/or LTh17 have promoted inflammation of epidermal keratinocytes.

The use of the ex vivo model of inflamed skin of the invention in methods for identifying compounds that modulate skin inflammation offers the advantages of relying on an easily produced model, that more accurately reflects the in vivo environment of inflamed skin, thereby reducing errors in screening tests for compounds in the form of false positives and/or false negatives.

Thus, the method according to the invention further aims at evaluating the anti-inflammatory efficacy of a compound and comprises the following additional steps:
 c) contacting, with a candidate compound, the ex vivo model of inflamed skin obtained at the end of step b) and comprising LTh1- and/or LTh17-polarized T cells;
 d) measuring the expression level of at least two inflammation markers of the ex vivo model of inflamed skin;
 e) comparing the expression level of said at least two inflammation markers obtained in step d) with their control expression level;
 f) identifying the anti-inflammatory efficacy of said candidate compound when the expression level of said at least two inflammation markers measured in step d) is lower than their control expression level.

With the method of the invention, the search for effective anti-inflammatory drugs to treat skin inflammation, and particularly psoriasis, will be facilitated.

Yet another object of the invention relates to the use of an ex vivo model of inflamed skin obtained by the method of the invention for the purpose of screening anti-inflammatory candidate compounds, in particular candidate compounds likely to treat psoriasis.

Finally, another object of the invention relates to a kit for implementing the method of the invention, said kit comprising a healthy skin biopsy previously taken from a mammal, a composition A comprising an effective amount of an anti-CD3 antibody and an anti-CD28 antibody, and optionally IL-2, a composition B comprising at least one mixture of IL-1β, IL-23, and TGFβ, and optionally a device for infusion injection.

DRAWING DESCRIPTION

FIG. 1 illustrates the manual (M) or infusion (P) intradermal injection of a stained solution into a skin biopsy and its diffusion by comparing the gradient of staining intensity obtained by manual injection or infusion.

FIG. 2 compares the histological characteristics of a healthy skin biopsy that is untreated (C) or treated according to steps a) and b) of the method of the invention (Th17/Th1). The observations were made 5 days (T5) or 7 days (T7) after the incubation of the injected healthy skin biopsy from step a) of the method of the invention in the polarization solution started. After 7 days of culture in the presence of a composition comprising at least one mixture of IL-1β, IL-23, and TGFβ, spongiosis (S) in the epidermis and elongation of the epidermal ridges (E) were observed.

FIG. 3 illustrates the histological analysis of the presence of Langerhans cells (CD207), resident T cells (CD3), dendritic cells (HLA-DR), and mast cells (Tryptase) in a healthy skin biopsy untreated (TO) and maintained in culture for 7 days (T7).

FIG. 4 illustrates the secretion of pro-inflammatory cytokines IL-17A and IL-22 by the model of inflamed skin obtained by the method of the invention showing the presence of LTh17 and LTh1 in the models treated according to steps a) and b) of the method of the invention (Th17/Th1). An untreated healthy skin biopsy (1—NativeSkin®), a healthy skin biopsy cultured in the presence of the polarization cocktail of step b) of the method of the invention (2—NativeSkin®+pro Th17/Th1), a healthy skin biopsy treated according to steps a) and b) of the method of the invention (3—InflammaSkin®) are compared. Results are expressed in pg/ml.

FIG. 5 illustrates the histological characteristics of a healthy skin biopsy that is untreated (C) or treated according to step b) only (IL-1β-IL-23+TGFβ) or according to steps a) and b) (Anti-CD3+anti-CD28+IL-2+IL-1β+IL-23+TGFβ) of the method of the invention, and after 7 days of culture. These biopsies were either untreated (1), treated with a placebo gel (2), or a placebo cream (4), or treated with either of the two inflammation inhibitors betamethasone di-propionate (3) and the phosphodiesterase type 4 inhibitor (5). Only treatments with the inflammation inhibitors (3 and 5) lead to a total absence of histological abnormalities in the epidermis suggesting an inhibition of pro-inflammatory cytokine secretion, and therefore of LTh17/LTh1 cell differentiation.

FIG. 6 illustrates the inhibition of IL-17A protein synthesis as a prophylactic (A) or therapeutic (B) treatment. The model of inflamed skin obtained by the method of the invention that is untreated (1), or treated with the placebo gel (2), with the gel comprising betamethasone di-propionate (3), the placebo cream (4), or the cream comprising the PDE4 inhibitor (5), are compared. The results are expressed in % in relation to the model of inflamed skin obtained by the method of the invention and left untreated (1).

FIG. 7 illustrates the inhibition of IL-22 protein synthesis as a prophylactic (A) or therapeutic (B) treatment. The model of inflamed skin obtained by the method of the invention that is untreated (1), or treated with the placebo gel (2), with the gel comprising betamethasone di-propionate (3), the placebo cream (4), or the cream comprising the PDE4 inhibitor (5), are compared. The results are expressed in % in relation to the model of inflamed skin obtained by the method of the invention and left untreated (1).

FIG. 8 illustrates the inhibition of IFNγ protein synthesis as a prophylactic (A) or therapeutic (B) treatment. The model of inflamed skin obtained by the method of the invention that is untreated (1), or treated with the placebo gel (2), with the gel comprising betamethasone di-propionate (3), the placebo cream (4), or the cream comprising the PDE4 inhibitor (5), are compared. The results are expressed in % in relation to the model of inflamed skin obtained by the method of the invention and left untreated (1).

FIG. 9 illustrates the inhibition of TNFα protein synthesis as a prophylactic (A) or therapeutic (B) treatment. The model of inflamed skin obtained by the method of the invention that is untreated (1), or treated with the placebo gel (2), with the gel comprising betamethasone di-propionate (3), the placebo cream (4), or the cream comprising the PDE4 inhibitor (5), are compared. The results are expressed in % in relation to the model of inflamed skin obtained by the method of the invention and left untreated (1).

FIG. 10 is a schematic representation of the ex vivo model of inflamed skin obtained by the method of the invention. A cell culture insert (10), the bottom of which consists of a porous membrane (40), contains the ex vivo model of inflamed skin (30) embedded in a solidified matrix (20). In a particular embodiment, the cell culture insert has lugs (60) and a ring consisting of a hydrophobic material (50) attached to the epidermal surface of said ex vivo model of inflamed skin.

FIG. 11 illustrates the ability of an anti-CD3 antibody to incorporate dermal cells of a human skin biopsy. The injection of the anti-CD3e antibody directly into the dermis of the biopsy (Intradermal Injection (II)—left panels), and the diffusion of the anti-CD3e antibody placed in the culture medium in which the skin biopsy floats (Addition to the culture medium (AMC)—right panels), are compared. Two separate biopsies were tested (replicates (R) 1 and 2). The white arrows identify the dermal cells that have incorporated the anti-CD3 antibody. The white star shows the presence of the anti-CD3 antibody on the epidermal surface of one of the skin biopsies (top right panel).

DETAILED DESCRIPTION OF THE INVENTION

Figure 1:
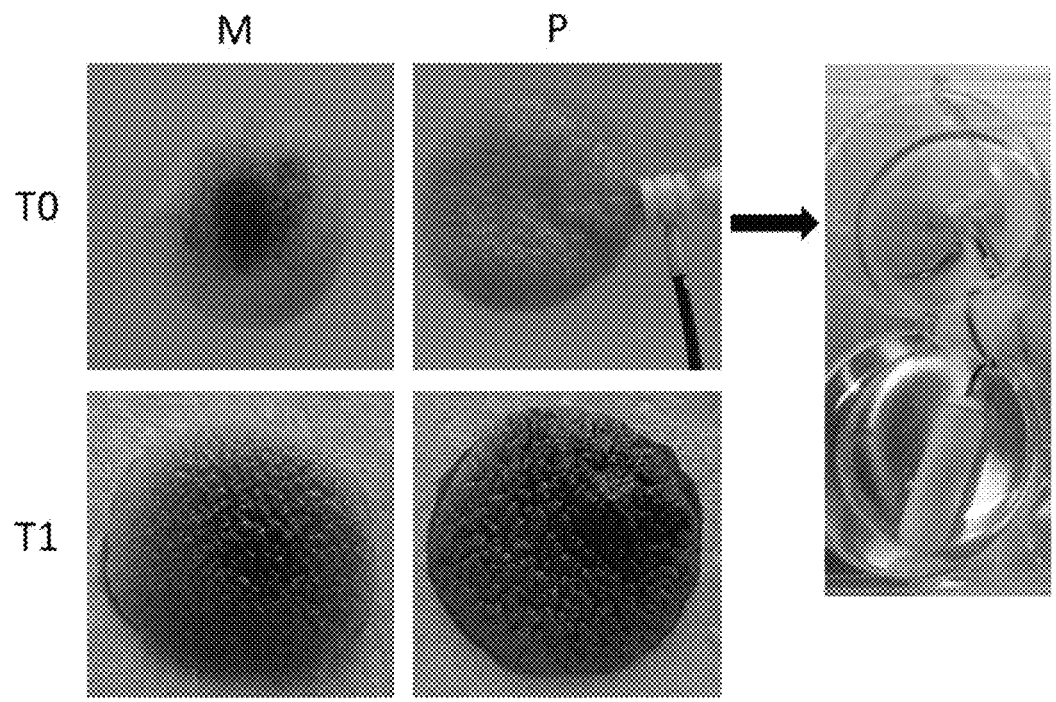

The invention aims to provide a new tool for evaluating the activity of a compound on the reduction of skin inflammation.

A first object of the invention relates to an in vitro method for obtaining an ex vivo model of inflamed skin comprising the following steps:
  a) injecting into the dermis of a healthy skin biopsy previously taken from a mammal a composition comprising an effective amount for activating dermal resident T cells of an anti-CD3 antibody and an anti-CD28 antibody, and optionally IL-2,
  b) incubating the injected skin biopsy obtained in step a) in the presence of a composition comprising an effective amount, for obtaining the polarization of the T cells activated in step a) into LTh1 and/or LTh17 and the synthesis of inflammation markers, of at least one mixture of IL-1β, IL-23, and TGF-β.

By "ex vivo model of inflamed skin" is meant a biopsy of skin with inflammatory characteristics. The identification of these inflammatory characteristics is based on the detection of the expression of inflammation markers at the protein or gene level. Inflammation markers include, but are not limited to, cytokines, antibacterial proteins, proteins involved in lipid biosynthesis, or any other molecule the expression level of which varies between an inflamed and a non-inflamed state (see in particular SERHAN & WARD, Molecular and Cellular Basis of Inflammation, Humana Press). Interleukins include, but are not limited to, IL-1A, IL-1B, IL-5, IL-7, IL-8, IL-9, IL-10, IL-12, IL-17A, IL-17C, IL-17F, IL-19, IL-21, IL-22, IL-23, IL-27, IL-31, and IL-33, as well as interleukin receptors including, but not limited to, IL-10RA, IL-10RB, IL-1R1, IL-5RA (CD125), and IL-9R. Chemokines also include, but are not limited to, C5, eotaxin, MCP-4, TARC, MCP-1, MIP-3A, CCL22, CCL23, MIP-1B, RANTES, MCP-3, MCP-2, CX3CL1, IL8RA, INP10, L8RB, and CXCL3, as well as chemokine receptors including, but not limited to, CCL13 (MCP-4), CCR1, CCR2, CCR3, CCR4, CCR5, CCR6, CCR8, CX3CR1, CXCR1, and CXCR2. In addition, other cytokines are possible, such as, but not limited to, MCP-1, GM-CSF, TNFSF5, MCSF, GCSF, TNFSF6, IFNA2, IFNG, TNFA, TNFB, MIF, NAMPT, TRAIL, and IFNA1, as well as other genes involved in inflammation including, but not limited to, CD4, CD40, TNFSF5, FASLG, JAK2, JNK1, NFkB, RAG1, STAT1, 5100 family proteins, and beta defensin.

Preferably, the ex vivo model of skin obtained by the method of the invention is considered to be an ex vivo model of inflamed skin when the expression rates of at least two, preferably at least three, and particularly preferably at least four inflammation markers selected from among those mentioned above are higher than those observed in a healthy skin biopsy (not inflamed and/or not having undergone the steps of the method according to the invention).

Preferably still, the ex vivo model of inflamed skin obtained by the method of the invention is comparable to the psoriatic lesions observed in a psoriasis patient when, in addition to the inflammation markers, overexpression of at least one gene or its product is detected among the 50 listed in Table S1 of the article by Yao et al., PloSOne, 2008, 3(7), e2737 and which are incorporated herein by reference.

In a particularly preferred manner, the ex vivo model of inflamed skin obtained by the method of the invention has protein and/or gene expression rates of at least three, preferably at least four, preferably at least five, and particularly preferably at least six inflammation markers selected from IL-8, IL-17A, IL-22, IL-23, IFNγ, TNFα, S100A7, S100A8, S100A9, S100A12, SERPINB3, SERPINB4, SERPINB13, DEFB4, KRT6A, KRT16, KRT17, CXCL9, CXCL10, CCL18, and CCL20 which are higher than those observed in a healthy skin biopsy.

In addition to the presence of inflammation markers or the overexpression of other aforementioned markers, physiological changes are also observable in the ex vivo model of inflamed skin obtained by the method of the invention. These include, but are not limited to, spongiosis of the epidermis, elongation of epidermal ridges in the dermis, the presence of pyknotic nuclei and cytoplasmic vacuolation in epidermal cells, and even detachments suggesting cell death caused by inflammation.

By "skin biopsy" is meant a skin fragment that comprises at least the epidermis, dermis, and epidermal appendages. This skin fragment or biopsy may also comprise a portion of the subcutaneous tissue also called the hypodermis. The hypodermis is located immediately below the dermis and forms a protective cushion separating the skin from the fibrous membranes surrounding the deeper organs, muscles, tendons, and bones. The hypodermis consists of adipocytes, nerves, a network of blood and lymphatic capillaries, a small number of fibroblasts involved in the synthesis of extracellular matrix components, and immune cells such as dendritic cells and macrophages. The hypodermis is divided into adipose lobules containing adipocytes and separated by connective walls that allow the passage of nerves and vessels. The functions of the hypodermis are to isolate, to provide a reserve of energy to the skin cells, and to absorb physical stress. In addition, studies have shown the important role played by lymphatic transport in the absorption of peptide-based drugs.

Preferably, the skin biopsy has a thickness ranging from 1 millimeter (mm) to 1 centimeter (cm), more particularly from 3 mm to 1 cm, even more particularly from 3 mm to 8 mm, and even more particularly from 5 mm to 7 mm. A thickness of up to 1 cm is obtained for skin biopsies comprising the epidermis, dermis, epidermal appendages, and hypodermis. In all cases, the thickness of the skin biopsy is not less than 1 mm.

Preferably said skin biopsy is taken from an animal, in particular a mammal, and preferably from a human. As biopsies that can be used in the method of the invention may be mentioned those obtained from surgical waste or slaughterhouses. By "surgical waste" is meant skin samples obtained from cosmetic surgery, including post-blepharoplasty, rhinoplasty, abdominoplasty, or breast reduction. Skin biopsy sampling techniques are well known to the one skilled in the art.

In order to ensure its in vitro survival, sampling must have been carried out within 1 h to less than 72 h, preferably within 1 h to less than 48 h, before injecting a composition comprising an effective amount of an anti-CD3 antibody and an anti-CD28 antibody, and optionally IL-2.

By "healthy skin biopsy" is meant a skin fragment that does not show any sign of inflammation perceptible to the eye (namely break in the skin, redness, swelling, heat, or excessive scaling . . . ), or express any inflammation marker. Furthermore, it is imperative that the healthy skin biopsy used in the method of the invention be taken from an individual with no dermatological pathology, in particular inflammatory.

Preferably, the skin biopsy has a cylindrical shape.

However, any other geometrical shape of the skin biopsy is also suitable for the method according to the invention, in particular a shape which is square, rectangular, oval, triangular, etc.

Preferably, the cylindrical shape has a diameter ranging from 1 mm to 50 mm, more particularly from 5 mm to 20 mm, even more particularly from 7 mm to 17 mm, and a thickness varying from 1 mm to 20 mm, more particularly from 2 mm to 15 mm, even more particularly from 2 mm to 10 mm, and even more particularly from 2 mm to 5 mm.

By "dermis" is meant the underlying tissue of the epidermis which contains dense vascular and nervous networks, as well as keratinized appendages extending the epidermis, the tissue also including hair follicles, sebaceous glands, and sweat glands.

The dermis is subdivided into two parts which differ in the composition and organization of their respective extracellular matrix. The papillary dermis lies directly under the epidermis. It is a loose connective tissue consisting of fine fibrils of type I and III collagen, and elastic fibers which are oriented perpendicular to the epidermis, thereby forming candle-shaped structures. The reticular dermis, placed under the papillary dermis, is also a connective tissue composed of interweaving bundles of large collagen fibers and elastic fibers which are preferentially oriented parallel to the skin surface. The reticular dermis contains less type III collagen than the papillary dermis.

By "inject into the dermis" is meant the injection, introduction or inoculation of a composition directly into the dermal structure of a healthy skin biopsy. This injection into the dermis is carried out using an injection device, in particular a hollow needle, beveled or not, with no dead volume, or any other equivalent mechanical device known to the one skilled in the art.

Preferably, the injection is carried out in the reticular dermis in order to avoid any trauma to the epidermis. In the skin biopsies used in the method of the invention, the presence under the dermis of the epidermal appendages and optionally of the hypodermis gives them a thickness limiting the risk of tearing during an injection.

Injection into the dermis of the biopsies from document WO 2014/182655 A1 would present an increased risk of tearing since these dermatomed biopsies without hypodermis are 750 µm thick (SMITH et al., PLoS One. 2016 Feb. 12; 11(2):e0147979).

The main advantage of injecting a composition directly into the dermal structure of a healthy skin biopsy is to allow a more homogeneous and faster diffusion of this composition into all tissues of the biopsy, and consequently a better activation of the resident T cells of the dermis. Such performance cannot be achieved by simple passive diffusion of the composition as used in document WO 2014/182655 A1.

Preferably still, the injection step is carried out at room temperature.

The volume of the composition injected into the dermis varies according to the size or surface area of the healthy skin biopsy, particularly its diameter if the latter has a cylindrical shape.

Preferably, when the diameter of the healthy skin biopsy is less than or equal to 8 mm, the volume of composition injected is less than or equal to 10 µl.

Preferably, when the diameter of the healthy skin biopsy is less than or equal to 15 mm, the volume of composition injected is less than or equal to 35 µl.

Preferably, the volume of the injected composition is at least 5 µl.

It is important, when injecting, not to damage the epidermis. Such a result can only be obtained if the skin biopsy has a thickness of at least 1 mm, preferably at least 2 mm, and more preferably at least 3 mm.

Preferably, the injection of the composition can be carried out manually or by infusion.

According to a particular embodiment, the injection of the composition comprising an effective amount of an anti-CD3 antibody and an anti-CD28 antibody, and optionally IL-2 into the dermis of the healthy skin biopsy is carried out manually.

Injection of the composition comprising an anti-CD3 antibody and an anti-CD28 antibody, and optionally IL-2 into the dermis of the healthy skin biopsy allows incorporation of the anti-CD3 and anti-CD28 antibodies, and optionally IL-2 into the dermal cells.

According to another particular embodiment, the injection of the composition comprising an effective amount of an anti-CD3 antibody and an anti-CD28 antibody, and optionally IL-2 into the dermis of the healthy skin biopsy is carried out by infusion, at a flow rate ranging from 4 to 12 µL/hour. In this particular embodiment, the injection can last several hours. In order to ensure a constant flow rate, the use of an osmotic pump or any other controlled liquid diffusion system is possible.

Contrary to a manual injection, injection by perfusion allows a more homogeneous diffusion of the composition in the dermis of the skin biopsy. By "more homogeneous diffusion" is meant a reduction in the concentration gradient of the compounds in the composition from the injection site to the edge (namely the outer diameter) of the biopsy. In addition, injection by infusion ensures better reproducibility.

By "anti-CD3 antibody" is meant any antibody or fragment thereof capable of specifically binding the CD3 antigen. CD3 is a membrane protein complex present at the surface of naive T cells and consists of one γ chain, one δ chain, and two ε chains. By associating with the T cell receptor (TCR) and with a complementary chain ζ, CD3 allows the formation of the TCR complex capable of transducing an intracellular signal. There are commercial forms of the anti-CD3 antibody, e.g. clone UCHT1 (THERMO FISHER 16-0038-81, MERCK MILLIPORE CBL150), or clone APA1/1 (MERCK MILLIPORE 05-785, THERMO FISHER MA1-10182).

Preferably, the concentration of anti-CD3 antibodies in the composition injected in step a) ranges from 10 ng/µl to 100 ng/µl, preferably from 20 ng/µl to 80 ng/µl, and particularly preferably from 30 ng/µl to 70 ng/µl.

According to a particular embodiment, the concentration of anti-CD3 antibody in the composition injected in step a) is 50 ng/µl.

By "anti-CD28 antibody" is meant any antibody or fragment thereof capable of specifically binding the CD28 antigen. CD28 is a co-stimulation protein present in particular at the surface of T cells and involved in their survival, their clonal expansion, their metabolic activity, as well as IL-2 production. There are commercial forms of the anti-CD28 antibody, e.g. clone 15E8 (MILTENYI BIOTEC 130-093-375) or clone CD28.6 (THERMO FISHER 16-0288-81).

Preferably, the concentration of anti-CD28 antibodies in the composition injected in step a) ranges from 10 ng/µl to 100 ng/µl, preferably from 20 ng/µl to 80 ng/µl, and particularly preferably from 30 ng/µl to 70 ng/µl.

According to a particular embodiment, the concentration of anti-CD28 antibody in the composition injected in step a) is 50 ng/µl.

According to a more particular embodiment, the anti-CD3 antibody and the anti-CD28 antibody are replaced by a single bispecific antibody having a first ScFV fragment specifically directed against CD3 and a second ScFV fragment specifically directed against CD28. This bispecific antibody has binding activities to both CD3 and CD28 antigens and resident T cell activation functions comparable to those of the anti-CD3 and anti-CD28 monospecific antibodies.

By "IL-2" is meant interleukin-2, which is a cytokine acting on mitosis and therefore on the proliferation of cells carrying the IL-2 receptor, in particular T helper cells.

Preferably, the concentration of IL-2 in the composition injected in step a) ranges from 1 ng/ml to 20 ng/ml, preferably from 2 ng/ml to 15 ng/ml, and particularly preferably from 4 ng/ml to 12 ng/ml.

According to a particular embodiment, the IL-2 concentration in the composition injected in step a) is equal to 10 ng/ml.

Within hours after injection of the composition comprising an anti-CD3 antibody and an anti-CD28 antibody, and optionally IL-2 into the dermis of the healthy skin biopsy, subpopulations of resident memory or naive $CD4^+$ and/or $CD8^+$ T cells in the dermis are activated, and potentially amplified. As these cells are in small numbers and randomly distributed in the dermis, it is important that the composition diffuses homogeneously throughout the dermis, and optionally into the epidermis of the biopsy.

By "effective quantity" is meant an amount that is sufficient to achieve the expected effect. This concept of effective amount is applicable to the anti-CD3 antibody, the anti-CD28 antibody, and also to IL-2. Within the meaning of the present invention and in connection with step a), the "expected effect" is the activation of dermal resident T cells in the dermis. This effect is enhanced when the injection of the composition is via infusion.

Activation of resident T cells in the dermis can be highlighted directly using activation markers, such as, but not limited to, CD69.

The effective amounts of anti-CD3 antibody, anti-CD28 antibody, and IL-2 vary according to the size of the skin biopsy.

As an example of an effective quantity may be mentioned the use of injection volumes in relation to the concentrations listed above.

According to a particular embodiment, the effective amounts of anti-CD3 antibody, anti-CD28 antibody, and IL-2 in the composition injected into the dermis of the healthy skin biopsy in step a) of the method of the invention are 500 ng, 500 ng, and 0.1 ng, respectively, for a biopsy with a diameter equal to 8 mm.

According to another particular embodiment, the effective amounts of anti-CD3 antibody, anti-CD28 antibody, and IL-2 in the composition injected into the dermis of the healthy skin biopsy in step a) of the method of the invention are 1750 ng, 1750 ng, and 0.35 ng, respectively, for a biopsy with a diameter equal to 15 mm.

According to a particular embodiment, the in vitro method according to the invention comprises, prior to step b), a step a') of depositing the injected skin biopsy obtained at the end of step a) on a liquid matrix capable of solidifying, said matrix being itself contained in a cell culture insert the bottom of which consists of a porous membrane and said insert being arranged in a container or well, so as to allow, once the matrix has solidified, the 3D integrity of the skin biopsy to be maintained.

By "liquid matrix capable of solidifying" is meant any liquid solution comprising at least one specific compound or composition the concentration of which in said liquid solution is such that, when implementing suitable conditions, especially particular temperature conditions, the liquid solution takes on a solid or gel-like consistency. Said specific compound or composition may be of animal, vegetable or synthetic origin, its nature and its concentration are determined according to the desired physicochemical characteristics of the matrix when solidified, especially the flexibility and strength of the matrix.

According to an embodiment of the method according to the invention, in step a'), said liquid matrix capable of solidifying is selected among any liquid solution, preferably nutritive, capable of solidifying or gelling under particular conditions compatible with the survival and the culture of skin cells constituting said skin biopsy, preferably selected from blood plasma or a solution derived from blood plasma, in particular diluted as a physiological buffer to a maximum of 10%, preferably to at least 20%, to at least 30% and 40%, a fibrinogen solution, a collagen solution, gelatin, synthetic polymeric gels, natural gels, such as agarose gels, in particular agarose or agar-agar gels with low melting points, starch or polysaccharide gels, or a mixture thereof.

Matrices capable of solidifying and methods for placing skin biopsies therein are detailed in European patent application EP 2 882 290 A1 and are incorporated herein by reference.

The purpose of the matrix capable of solidifying is to allow the injected skin biopsy obtained at the end of step a) of the method of the invention to be cultured, and easier handling thereof. By "cultured" is meant the maintenance of the physiological and morphological state of the skin biopsy, that is to say of all the tissues and cells constituting the biopsy.

The purpose of the matrix capable of solidifying is also to allow the skin biopsy in which the resident T cells have been activated by the method according to the invention to be preserved and/or transported.

The nature of the matrix capable of solidifying must allow the skin biopsy cells to remain alive, that is to say not have any cytotoxic effect and have a solidification/polymerization temperature at room temperature (namely from 15° C. to 25° C.).

In one particular embodiment, the matrix capable of solidifying is a solution of human fibrinogen.

According to a particular embodiment, the in vitro method according to the invention comprises, prior to step a'), a step a'') of attaching, to the epidermal surface of the injected skin biopsy obtained at the end of step a), a ring, or disc perforated at its center, consisting of a hydrophobic material, the external diameter of said ring being greater than the diameter of the epidermal surface of the skin biopsy and the internal diameter of said ring being less than the diameter of the epidermal surface of the skin biopsy.

Preferably, the hydrophobic material of the ring is a material that is not toxic to the skin, it may be a paraffin polymer, such as a Parafilm® (SIGMA), or a silicon polymer. According to a particular mode, the ring is prepared from a film of hydrophobic material, by perforating said film according to the desired dimensions. The thickness of the ring is preferably between 0.1 mm and 2 mm, preferably between 0.1 and 1 mm, more preferably between 0.1 and 0.5 mm, and even more preferably between 0.12 and 0.2 mm.

Said ring may be made of an opaque or translucent material. According to a particular embodiment, the ring is made of an opaque material.

According to a more particular embodiment, said ring is attached to the epidermal surface of the biopsy using glue, preferably added to the lower surface of the ring. Said glue can be selected from any type of material that is not toxic to the skin and which has the effect of adhering the ring to the skin, where this material may be silicon. Preferably, said glue is hydrophobic.

The materials, glues and attachment methods of this hydrophobic ring are detailed in European patent application EP 2 882 290 A1 and are incorporated herein by reference.

By "incubate the injected skin biopsy obtained in step a)" is meant the step of placing the skin biopsy previously injected at the dermis with the composition comprising an effective amount of anti-CD3 antibody and anti-CD28 antibody, and optionally IL-2 in a culture medium containing all the elements necessary for its survival. Step b) is therefore carried out by contacting the skin biopsy obtained at the end of step a) with a culture medium containing all the elements necessary for its survival.

In this step b), the resident T cells in the dermis which have been activated at the end of step a) are additionally polarized into LTh1 and/or LTh17 cells. By "polarize" is meant the differentiation of activated resident T cells into LTh1 and/or LTh17 T helper cell lineages.

By "Th1 cells" is meant the subpopulation of T cells derived from the differentiation of naive $CD4^+$ T cells under the effect of the cytokines IL-12 and IFN-γ and which possess a cytokine synthesis profile specific to this subpopulation, namely IFN-γ, TNF-α, and IL-2.

By "Th17 cells" is meant the subpopulation of T cells derived from the differentiation of memory or naive CD4$^+$ and/or CD8$^+$ T cells under the effect of the cytokines TGF-β, IL-6, IL-1, and IL-23 and which have a cytokine synthesis profile specific to this subpopulation, namely IL-17, and IL-22.

The measurement of the production of cytokines specific to these two cell subpopulations Th1 and/or Th17 is directly correlated to the numbers of these cells.

This differentiation is induced by adding to the culture medium healthy skin biopsies previously injected as defined in step a) of the method of the invention, a composition comprising an effective amount of at least one mixture of interleukin-1beta (IL-1β), interleukin-23 (IL-23), and transforming growth factor beta (TGF-β).

By "interleukin-1beta" is meant a protein of approximately 30 kDa derived from caspase 1 proteolysis of a precursor naturally secreted by macrophages and dendritic cells in response to a bacterial attack. This cytokine is an important mediator of the inflammatory response and is involved in many cellular activities including proliferation, differentiation, and apoptosis.

By "interleukin-23" is meant a heterodimeric protein of about 60 kDa composed of a p19 subunit specific to IL-23, and a p40 subunit common to IL-12. By binding to a heterodimeric receptor IL12RB1 and IL23R present at the surface of some subpopulations of T cells, this cytokine allows the stimulation of memory T cells leading to the synthesis of pro-inflammatory cytokines.

By "TGF-β" is meant a 25 kDa dimeric protein corresponding to the mature form of a cytokine synthesized as a precursor. This cytokine is secreted by a large number of cells, including macrophages, and exerts pleiotropic effects on cells ranging from proliferation to apoptosis. TGF-β also plays a very important role in the regulation of inflammation.

By "effective amount", within the meaning of the present invention and in connection with step b) is meant an effective amount of IL-1β, IL-23, and TGF-β for obtaining the polarization of the T cells activated in step a) into LTh1 and/or LTh17, and the synthesis of inflammation markers.

Preferably, the concentration of IL-1β in the mixture of the composition used in step b) of the method of the invention ranges from 1 ng/ml to 50 ng/ml, preferably from 5 ng/ml to 30 ng/ml, and particularly preferably from 7 ng/ml to 15 ng/ml.

According to a particular embodiment, the concentration of IL-1β in the mixture of the composition used in step b) of the method of the invention is 10 ng/ml.

Preferably, the concentration of IL-23 in the mixture of the composition used in step b) of the method of the invention ranges from 10 ng/ml to 100 ng/ml, preferably from 20 ng/ml to 80 ng/ml, and particularly preferably from 30 ng/ml to 60 ng/ml.

According to a particular embodiment, the concentration of IL-23 in the mixture of the composition used in step b) of the method of the invention is 50 ng/ml.

Preferably, the TGF-β concentration in the mixture of the composition used in step b) of the method of the invention ranges from 1 ng/ml to 50 ng/ml, preferably from 5 ng/ml to 30 ng/ml, and particularly preferably from 7 ng/ml to 15 ng/ml.

According to a particular embodiment, the concentration of TGF-β in the mixture of the composition used in step b) of the method of the invention is 10 ng/ml.

According to a more particular embodiment, the concentrations of IL-1β, IL-23, and TGF-β in the mixture of the composition used in step b) of the method of the invention are 10 ng/ml, 50 ng/ml, and 10 ng/ml, respectively.

Step b) of the method of the invention is carried out at 37° C. in a $CO_2$ incubator for a period of time long enough to allow the polarization of activated TCD4$^+$ cells of the dermis into Th1 and/or Th17 cells.

Preferably, step b) of incubating the injected skin biopsy obtained in step a) in the presence of a composition comprising at least one mixture of IL-1β, IL-23, and TGFβ is carried out for a period of at least 3 days, preferably between 3 and 10 days.

Preferably, the incubation period of step b) of the method of the invention shall not be less than 5 days.

According to a particular embodiment, the duration of step b) of incubating the injected skin biopsy obtained in step a) in the presence of a composition comprising at least one mixture of IL-1β, IL-23, and TGF-β is 7 days.

Preferably, the composition comprising at least one mixture of IL-1β, IL-23, and TGF-β used in step b) of the method of the invention is frequently renewed in order to maintain a constant concentration of the components of the mixture, their half-life in solution being from a few minutes to a few hours.

According to a particular embodiment, the composition comprising at least one mixture of IL-1β, IL-23, and TGF-β used in step b) of the method of the invention is renewed daily throughout the duration of this step.

According to another particular embodiment, the method according to the invention further aims at evaluating the anti-inflammatory efficacy of a compound and comprises the following additional steps:

c) contacting, with a candidate compound, the model of inflamed skin obtained at the end of step b) comprising LTh1- and/or LTh17-polarized T cells;

d) measuring the expression level of at least two inflammation markers of the model of inflamed skin;

e) comparing the expression level of said at least two inflammation markers obtained in step d) with their control expression level;

f) identifying the anti-inflammatory efficacy of said candidate compound when the expression level of said at least two inflammation markers measured in step d) is lower than their control expression level.

By "anti-inflammatory efficacy" is meant the ability of a compound to reduce inflammation, such as, but not limited to, reducing the production of pro-inflammatory cytokines, promoting the synthesis of anti-inflammatory cytokines, modulating the proliferation of immune system cells.

By "candidate compound" is meant any synthetic or natural chemical selected for its potential use as an inflammation modulator. Candidate compounds can be purified or mixed. Candidate compounds include small molecules, macromolecules, and polymers. In some embodiments, a candidate compound may be a molecule produced by chemical synthesis or contained in a combinatorial library. In some embodiments, a candidate compound may be a molecule or macromolecule the structure of which is designed by computer or a three-dimensional analysis. The candidate compound also includes crude or purified extracts from organic sources (e.g. animal extracts, plant extracts, and microbial lysates). The candidate compounds used in the implementation of the method of the invention may be combined with an inert buffer (e.g. a salt solution) or an appropriate solvent (e.g. dimethylsulfoxide (DMSO), alcohols, such as methanol and ethanol, aqueous solutions or any other compound used in cosmetic compositions.

By "inflammation marker" is meant an expressible element, or the element expressed thereby, showing a change in the expression level in a cell, tissue or organ that is inflamed compared to a cell, tissue or organ that is not inflamed. Some inflammation markers show statistically significant differences (p≤0.10) in the expression level in inflamed cells, tissues or organs compared to non-inflamed cells, tissues or organs. For example, an "inflammation marker" may be a gene, gene fragment, or coding region expressed at a different rate in cells contained in an inflamed tissue compared to cells of the same type contained in a similar tissue that is not inflamed. An "inflammation marker" may correspond to an RNA (e.g. mRNA) production or a protein production, measured by the physical presence of the protein or by an activity characteristic of the protein. A list of inflammation markers is provided earlier in the description.

Depending on the nature of the inflammation marker (mRNA or protein), detection methods well known to the one skilled in the art will be applied. These include, but are not limited to, western blots or ELISA-type tests for the detection of proteins. The mRNA expression of the genes of interest can be determined using microarray, RNA-Seq or NextGen sequencing techniques. It is also possible to measure the inflammation markers directly in the culture medium of the model of inflamed skin, in all or part of the model of inflamed skin, or specifically in the dermis or epidermis, or in certain cell subtypes of the dermis and/or epidermis.

Contacting the candidate compound with the model of inflamed skin in step c) can be carried out topically or directly in the culture medium. In the case of a topical application, the epidermal surface of the ex vivo model of inflamed skin obtained from steps a) and b) of the method of the invention is dried (namely the possible traces of liquid from the epidermis are removed) prior to the application of the candidate compound.

It is also possible that this step of contacting the candidate compound with the model of inflamed skin in step c) be carried out by subcutaneous injection. Such an embodiment is particularly appropriate for candidate compounds that have a high molecular weight, are highly hydrophilic, or are easily degraded. By way of example, such compounds may be candidate compounds of a proteinaceous nature, in particular antibodies.

Preferably, step c) of contacting the candidate compound with the model of inflamed skin may last from a few minutes to a few hours, or even days. Depending on the nature, stability, solubility, or any other physicochemical property of the candidate compound, said contacting may also be renewed daily for a total duration of 7 days.

Preferably, in step d) of the method of the invention, the expression level of at least three, preferably at least four, and particularly preferably at least five inflammation markers will be measured.

The inflammation markers are as previously defined.

According to a particular embodiment, step d) also includes measuring the expression level of at least three, preferably at least four, in particular at least five and, particularly preferably at least six inflammation markers selected from the group consisting of IL-8, IL-17A, IL-22, IL-23, IFNγ, TNFα, S100A7, S100A8, S100A9, S100A12, SERPINB3, SERPINB4, SERPINB13, DEFB4, KRT6A, KRT16, KRT17, CXCL9, CXCL10, CCL18, and CCL20.

The control expression level may be measured in the model of inflamed skin obtained by the method of the invention in step b), and prior to step c) of contacting it with the candidate compound.

The control expression level may also be measured in one or more samples of inflamed skin, particularly with psoriatic lesions, taken from one or more patients with inflammatory skin conditions, particularly psoriasis.

Preferably, at the end of step f) of the method of the invention, candidate compounds which are associated with a decrease in the levels of protein and/or gene expression of the at least two inflammation markers by at least 10%, preferably by at least 30%, preferably by at least 50%, and particularly preferably by at least 80%, will be selected.

Such a method makes it possible to identify compounds having a therapeutic effect on an existing inflammation.

Such an effect cannot be measured with the model developed in document WO 2014/182655 A1. Indeed, it seems that this model can only be analyzed at best 48 hours after activation of the resident T cells of the dermis.

It is also possible to test the effectiveness of a compound in preventing inflammation from occurring.

According to yet another particular embodiment, steps b) and c) of the method of the invention are carried out simultaneously so as to prevent the onset of inflammation in the event that the candidate compound under test has an anti-inflammatory effect.

It is also possible to test the prophylactic efficacy of a compound.

In this case, the order of steps a), b) and c) of the method of the invention is reversed so as to prevent the onset of inflammation. In this embodiment, contacting the candidate compound with the skin model takes place prior to steps a) of activating and b) of polarizing the resident T cells in the dermis.

The method of the invention can also be used in addition to other screening tests for candidate compounds modulating skin inflammation, such as, but not limited to, in vitro tests on skin cell subpopulations, enzymatic tests, or even ex vivo tests carried out on skin biopsies from patients with an inflammatory skin disease (namely dermatitis, psoriatic lesions . . . ).

A further object of the invention relates to an ex vivo model of inflamed skin comprising a dermis, an epidermis, epidermal appendages, and optionally a hypodermis, and in which activated T cells polarized into LTh1 and/or LTh17 have promoted inflammation of epidermal keratinocytes.

Preferably, the ex vivo model of inflamed skin comprises a dermis, an epidermis, epidermal appendages, and Th1 and/or Th17 cells and is characterized by the expression of at least two inflammation markers and, optionally, keratinocyte hyperproliferation.

Preferably still, the ex vivo model of inflamed skin comprises a dermis, an epidermis, epidermal appendages, a hypodermis, and Th1 and/or Th17 cells and is characterized by the expression of at least two inflammation markers and, optionally, keratinocyte hyperproliferation.

The measurement of the expression of at least two inflammation markers can be carried out at the protein and/or gene level.

According to a preferred embodiment, the ex vivo model of inflamed skin comprises a dermis, an epidermis, epidermal appendages, and Th1 and/or Th17 cells and is characterized by the expression at the protein and/or gene level of at least two inflammation markers and at least three, in particular at least four, preferably at least five, and particularly preferably at least six inflammation markers selected from the group consisting of IL-8, IL-17A, IL-22, IL-23, IFNγ, TNFα, S100A7, S100A8, S100A9, S100A12, SERPINB3, SERPINB4, SERPINB13, DEFB4, KRT6A, KRT16, KRT17, CXCL9, CXCL10, CCL18, and CCL20.

According to another preferred embodiment, the ex vivo model of inflamed skin comprises a dermis, an epidermis, epidermal appendages, a hypodermis, and Th1 and/or Th17 cells and is characterized by the expression at the protein and/or gene level of at least two inflammation markers and at least three, in particular at least four, preferably at least five, and particularly preferably at least six inflammation markers selected from the group consisting of IL-8, IL-17A, IL-22, IL-23, IFNγ, TNFα, S100A7, S100A8, S100A9, S100A12, SERPINB3, SERPINB4, SERPINB13, DEFB4, KRT6A, KRT16, KRT17, CXCL9, CXCL10, CCL18, and CCL20.

In order to optimize its ex vivo survival maintenance, its handling and its transport, said ex vivo model of inflamed skin can be placed in a solidified matrix which maintains the epidermis in contact with air, said matrix being contained in a cell culture insert.

Another object of the invention relates to a cell culture insert (10), suitable for being contained in a container or a culture box well, and the bottom of which consists of a porous membrane (40), said insert containing the ex vivo model of inflamed skin (30) embedded in a solidified matrix (20), said matrix being in contact with the inner edge of the insert and the porous membrane, the epidermis of the ex vivo model of inflamed skin being in contact with the atmosphere and the dermis and the epidermal appendages of the ex vivo model of inflamed skin being immersed in the solidified matrix.

According to a particular embodiment, said cell culture insert the bottom of which consists of a porous membrane is an insert in the shape of a nacelle (namely a U), preferably the diameter of which ranges between 5 and 40 mm, more preferably between 9.5 and 30 mm.

According to another particular embodiment, said cell culture insert (10), suitable for being contained in a container or a culture box well, and the bottom of which consists of a porous membrane (40), contains the injected healthy skin biopsy obtained at the end of step a) of the method of the invention (30) embedded in a solidified matrix (20), said matrix being in contact with the inner edge of the insert and the porous membrane, the epidermis of the skin biopsy being in contact with the atmosphere and the dermis and the epidermal appendages of the skin biopsy being immersed in the solidified matrix. Optionally, the solidified matrix also contains at least the mixture of IL-1β, IL-23, and TGF-β.

Preferably still, said cell culture insert is an insert that is suspended or on piles, preferably suspended by means of lugs (60).

According to another particular embodiment, a hydrophobic ring (50) is attached to the epidermal surface of the ex vivo model of inflamed skin.

Preferably still, said porous membrane is a membrane with a porosity for preventing the liquid matrix from flowing through the membrane before solidification thereof, preferably ranging between 0.4 and 8 µm, more preferably between 0.4 and 1.5 µm, between 0.8 µm and 1.2 µm being the preferred porosity.

Preferably still, said porous membrane is a membrane selected from polyethylene terephthalate (PET), nitrocellulose, or polycarbonate.

Among cell culture inserts may be mentioned those supplied in particular by the NUNC company (Roskilde, Danemark), BD Falcon (BECTON DICKINSON France SAS, 38 801 Le Pont-De-Claix, France), Millicell® (EMD MILLIPORE CORPORATION, Billerica, Mass., USA), or Costar® (Grosseron SAS, 44819 Saint-Herblain France), for example the inserts with a membrane made of polycarbonate, PET or nitrocellulose pre-packaged in multi-well plates with 6, 8, 12, and 24 wells, the membrane porosity of which may vary between 0.4 and 8 µm, where 8-well boxes and/or boxes with a membrane porosity of 0.8 µm to 1 µm and/or PET are the most preferred.

According to a particular embodiment, said container in which said cell culture insert is placed is a well of a cell culture plate with 6, 8, 12, 24, or 48 wells.

Among these culture plates may be mentioned those supplied in particular by NUNC, BD FALCON, or under the references Millicell® or Costar®.

Preferably, the bottom of the cell culture insert is located at a distance between 1 mm and 2.5 mm from the bottom of the container containing said insert, especially from the bottom of the well of the culture plate (or the bottom of the Petri dish depending on the designation).

An advantage of the model of inflamed skin of the invention is that it is possible to carry out screening for anti-inflammatory compounds on a large scale, in particular by repeatedly using samples (namely biopsies) of healthy skin from the same donor or separate donors. A plurality of candidate compounds can be screened, from tens to hundreds, or even thousands. One advantage of obtaining models of inflamed skin from several donors is to be able to compare the interindividual modulation of the rate of inflammation markers and thus identify the candidate compounds most active in reducing skin inflammation.

Yet another object of the invention relates to the use of the ex vivo model of inflamed skin obtainable by the method described above for identifying compounds with an anti-inflammatory effect.

The structure of the ex vivo model of inflamed skin obtainable by the method described above allows a proper diffusion of the compounds with an anti-inflammatory effect after subcutaneous injection or topical application, de facto influencing their bioavailability.

The compounds identified according to this use of the invention may serve as a basis for the development of therapeutic treatments for a patient with acute or chronic skin inflammation. Such a use according to the invention makes it possible to envisage a therapy that can be personalized from one patient to another according to the intensity of the anti-inflammatory effect of the various compounds tested on the models of inflamed skin obtained by the method of the invention.

Among inflammatory skin diseases may be mentioned, but with no limitation, atopic dermatitis, psoriasis, eczema, dermatoses, allergic contact dermatitis, lichen, pruritus, Netherton's syndrome, ichthyosis vulgaris . . . .

According to a particular embodiment of the invention, the ex vivo model of inflamed skin obtainable by the method described above allows compounds for treating psoriasis to be identified.

Another object of the invention relates to a kit for implementing the method of the invention, said kit comprising a healthy skin biopsy previously taken from a mammal, a composition A comprising an effective amount of an anti-CD3 antibody and an anti-CD28 antibody, and optionally IL-2, a composition B comprising at least one mixture of IL-1β, IL-23, and TGFβ, and optionally an injection device, in particular by infusion.

Preferably, the effective amount of anti-CD3 in composition A ranges from 10 ng/μl to 100 ng/μl, preferably from 20 ng/μl to 80 ng/μl, and particularly preferably from 30 ng/μl to 70 ng/μl.

Preferably, the effective amount of anti-CD28 in composition A ranges from 10 ng/μl to 100 ng/μl, preferably from 20 ng/μl to 80 ng/μl, and particularly preferably from 30 ng/μl to 70 ng/μl.

Preferably, the effective amount of IL-2 in composition A ranges from 1 ng/ml to 20 ng/ml, preferably from 2 ng/ml to 15 ng/ml, and particularly preferably from 4 ng/ml to 12 ng/ml.

According to a particular embodiment, the effective amounts of anti-CD3 antibody, anti-CD28 antibody, and IL-2 in composition A are 50 ng/μl, 50 ng/μl, and 10 ng/ml, respectively.

Preferably, the concentration of IL-1β in the mixture of composition B ranges from 1 ng/ml to 50 ng/ml, preferably from 5 ng/ml to 30 ng/ml, and particularly preferably from 7 ng/ml to 15 ng/ml.

Preferably, the IL-23 concentration in the mixture of composition B ranges from 10 ng/ml to 100 ng/ml, preferably from 20 ng/ml to 80 ng/ml, and particularly preferably from 30 ng/ml to 60 ng/ml.

Preferably, the TGF-β concentration in the mixture of composition B ranges from 1 ng/ml to 50 ng/ml, preferably from 5 ng/ml to 30 ng/ml, and particularly preferably from 7 ng/ml to 15 ng/ml.

According to a particular embodiment, the amounts of IL-1β, IL-23, and TGF-β in the mixture of composition B are 10 ng/ml, 50 ng/ml, and 10 ng/ml, respectively.

In a kit according to the invention, a healthy skin biopsy is taken from a skin fragment that does not show any sign of inflammation perceptible to the eye (namely break in the skin, redness, swelling, heat, or excessive scaling . . . ) or does not express any inflammation marker. In addition, said healthy skin biopsy comprises at least the epidermis, dermis, and epidermal appendages, and optionally a portion of the subcutaneous tissue also referred to as the hypodermis.

Preferably, said skin biopsy is taken from an animal, in particular a mammal, and preferably from a human. As biopsies that can be used in the kit of the invention may be mentioned those obtained from surgical waste or slaughterhouses. By "surgical waste" is meant skin explants obtained from cosmetic surgery, including post-blepharoplasty, rhinoplasty, abdominoplasty, or breast reduction. Skin biopsy sampling techniques are well known to the one skilled in the art.

In a kit according to the invention, the manual injection device comprises a syringe without a dead volume in the needle with a 26S or 22S format.

In a kit according to the invention, the infusion injection device comprises an osmotic pump connected to a catheter connected to a 28 G- or 30 G-format needle.

Yet another object of the invention relates to a kit comprising:
- at least one cell culture insert (10), suitable for being contained in a container or a culture box well, and the bottom of which consists of a porous membrane (40), said insert containing the injected healthy skin biopsy obtained at the end of step a) of the method of the invention (30) embedded in a solidified matrix (20), said matrix being in contact with the inner edge of the insert and the porous membrane, the epidermis of the skin biopsy being in contact with the atmosphere and the dermis and the epidermal appendages of the skin biopsy being immersed in the solidified matrix,
- a composition B comprising at least one mixture of IL-1β, IL-23, and TGF-β.

According to another particular embodiment, said kit of the invention comprises:
- at least one cell culture insert (10), suitable for being contained in a container or a culture box well, and the bottom of which consists of a porous membrane (40), said insert containing the injected healthy skin biopsy obtained at the end of step a) of the method of the invention (30) embedded in a solidified matrix (20) containing at least the mixture of IL-1β, IL-23, and TGF-β, said matrix being in contact with the inner edge of the insert and the porous membrane, the epidermis of the skin biopsy being in contact with the atmosphere and the dermis and the epidermal appendages of the skin biopsy being immersed in the solidified matrix,
- a composition B comprising at least one mixture of IL-1β, IL-23, and TGF-β.

The following examples are given solely by way of illustration of the subject matter of the present invention, and in no way constitute a limitation thereof.

EXAMPLES

1—Preparation of Skin Biopsies

The skin biopsies are prepared from a complete skin sample, including the epidermis, dermis, and hypodermis. Based on these biopsies, two different embodiments are possible depending on the nature of the anti-inflammatory compounds to be tested.

In a first embodiment, the adipose tissue (namely the hypodermis) is cut with curved scissors in order to separate it from the dermis. The biopsies (epidermis and dermis), the thickness of which is about 3 mm, are then cut out using a metal punch. This first embodiment is for testing anti-inflammatory compounds by a topical application.

In a second embodiment, the hypodermis is preserved. The biopsies (epidermis, dermis, and hypodermis), the thickness of which is about 1 cm, are then cut out using a metal punch. This second embodiment is for testing anti-inflammatory compounds by subcutaneous injection.

Once prepared, the biopsies are maintained floating in buffered saline until the resident T cell activation step.

2—Activation of Resident T Cells

Using a clamp, the skin biopsy is held flat, with the dermis on top. A needle with no dead volume is inserted into the biopsy from the side of the dermis using a 701N or 705N Hamilton syringe (for 8 mm or 15 mm diameter biopsies, respectively). 10 μL or 35 μL of the activation solution (50 ng/μL anti-CD3 antibody, 50 ng/μL anti-CD28 antibody, and 10 ng/mL IL-2) for biopsies of 8 or 15 mm diameter, respectively, are injected from the side of the biopsy to avoid damage to the epidermis.

When the injection is carried out by infusion, 200 μL of the activation solution are loaded into the osmotic pump (for the 2001D pump model tested). The concentration of the solution was adjusted according to the size of the biopsies: 2.5 ng/μL anti-CD3 antibody, 2.5 ng/μL anti-CD28 antibody, 0.5 ng/mL IL-2 for 8 mm diameter biopsies; 8.75 ng/μL anti-CD3 antibody, 8.75 ng/μL anti-CD28 antibody, 1.75 ng/mL IL-2 for 15 mm diameter biopsies.

The pump is then connected to a catheter using a flow moderator. The pump is then primed: it is placed in buffered saline and incubated at 37° C. for 3 hours.

At the end of this incubation, the free end of the catheter (not connected to the pump) is connected to a needle. Implantation of the needle into the dermis of the biopsy is carried out manually in the same way as described above: the skin is held flat with a clamp, with the dermis on top. The needle is inserted into the dermis from the side of the biopsy so as not to damage the epidermis.

The implanted biopsies are then deposited floating on an appropriate culture medium. The pumps are kept immersed in a buffered saline solution. All of it is incubated for 24 hours in an incubator at 37° C., 5% $CO_2$, and maximum humidity.

At the end of the 24 hours of infusion, the needle is removed from the biopsy and the pump is thus disconnected.

3—Ex Vivo Culture

The skin biopsy, the resident T cells of which have been activated, is mounted on a liquid matrix poured into a culture insert using the same method as that used for the Native-Skin® model, based on the use of a natural matrix as a physical support and nutrient layer for in vitro cultured human skin or epidermis explants. The explant is then cultured in plates (incubator culture, daily renewal of the culture medium).

4—Differentiation of T Cells into Th1/Th17

In WILLIAM'S E synthetic culture medium, the following supplements are added: 10 ng/mL IL-1β, 50 ng/mL IL-23, and 10 ng/mL TGFbeta. The culture is carried out for 7 days in a $CO_2$ incubator at 37° C. The culture medium containing the supplements is changed daily.

Following the activation and differentiation steps of resident T cells in the dermis, the skin biopsies have the trade names InflammaSkin® when they include the epidermis and dermis, or Hypo-InflammaSkin® when they include the epidermis, dermis, and hypodermis.

5—Histology Analysis 5.1—Microtome Cutting

The analysis can be carried out on samples included in a paraffin block by serial sections with a microtome.

The skin biopsy treated according to steps a) and b) of the method of the invention is dehydrated by an alcohol bath, and then passed through a xylene bath. A first bath in paraffin allows to replace the water previously contained in the skin explant by paraffin.

The paraffin-impregnated samples are taken out of their bath and transferred to a container, the bottom of which is lined with absorbent paper, to be taken to the vicinity of the embedding station.

The samples, enclosed in histology cassettes, are immersed in liquid paraffin at 56° C. to remelt the paraffin impregnating them.

For each sample: the histology cassette is opened, the sample is possibly cut in half. An embedding mold is filled with liquid paraffin, and the sample (or the 2 sample pieces) is placed in the mold and oriented in the desired direction for cutting. At the same time, the mold is transferred onto a refrigerated rack in order to solidify the paraffin at the bottom of the mold and hold the sample therein. The lid of the histology cassette with the sample reference placed on top is placed thereover, so that the paraffin passes therethrough (paraffin can be added where necessary), and then the assembly is placed in cold storage (refrigerator, freezer, cold room . . . ) for several minutes (5-6), in order to solidify the paraffin into a block, trapping the sample in the right orientation and the lid of the histology cassette which will become the support of the block.

Once the block is solid, it is released from the mold. Excess paraffin is possibly scraped off with a spatula on the sides of the lid of the embedding cassette.

Serial sections of a thickness varying from 4 to 5 μm are then made along the entire length of the paraffin block containing the sample.

Figure 2:
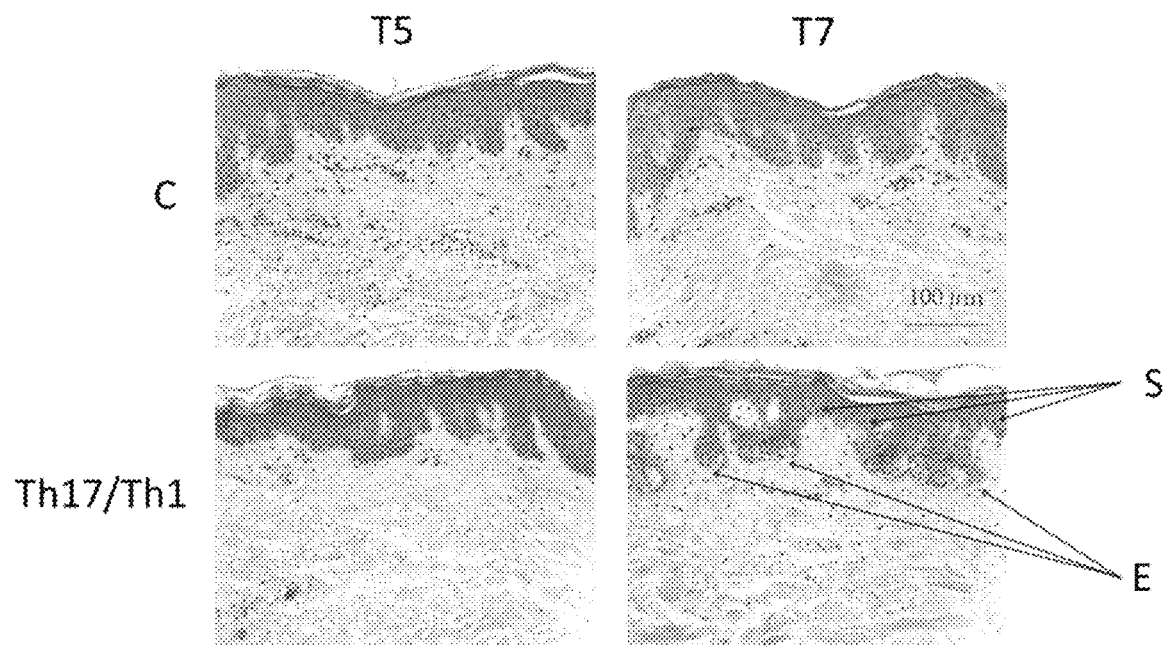

FIG. 2 illustrates the results of such staining performed on a skin biopsy treated according to the method of the invention after 5 or 7 days of culture in the polarization medium of resident T cells activated into Th1 and/or Th17 cells. Analysis of the model by histology (e.g. hematoxylin and eosin staining) allows to attest to the appearance of spongiosis (S) at the epidermis, as well as to the formation of epidermal ridge elongation (E) after 7 days of culture of the biopsies activated in a polarization medium.

Figure 3:
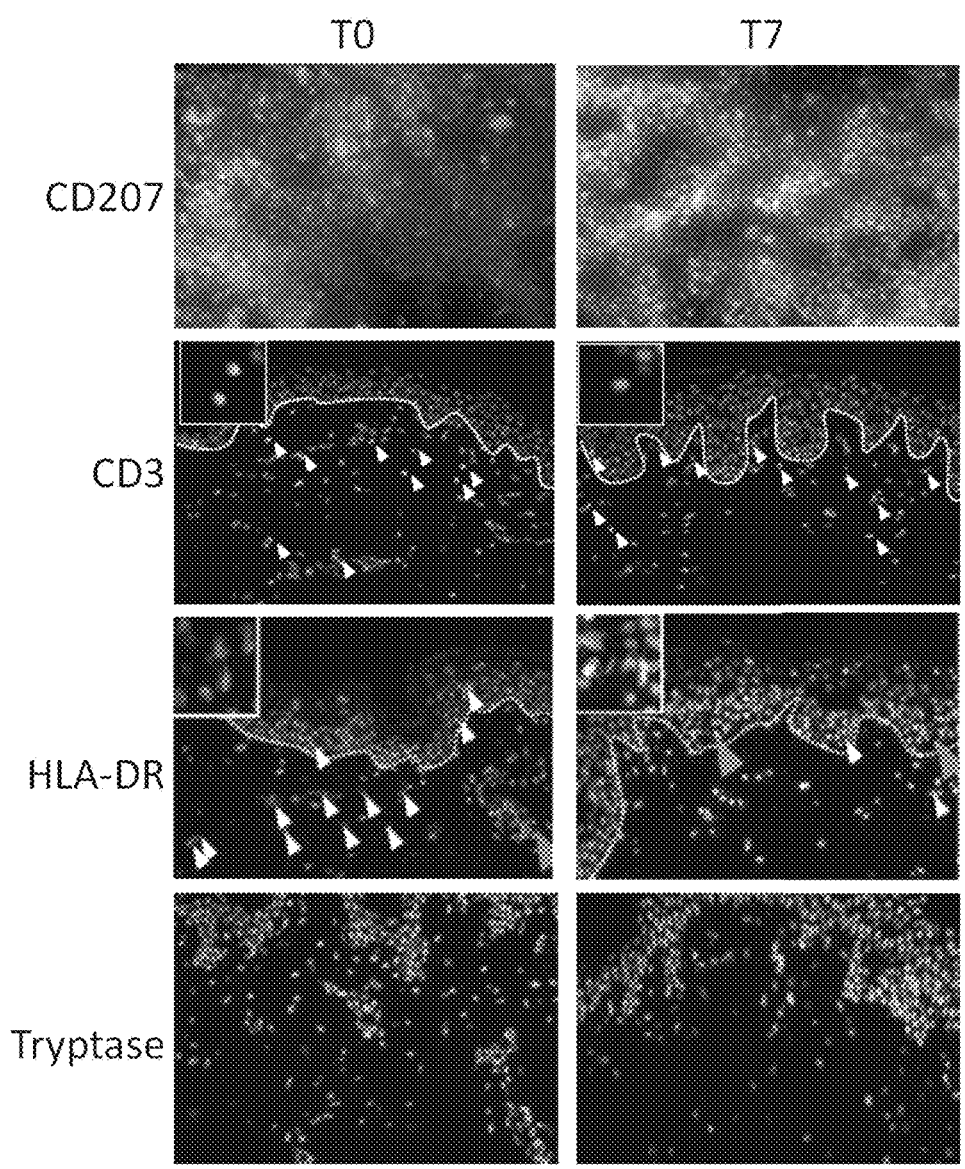

Analyses were carried out in histology using anti-CD207, anti-CD3, anti-HLA-DR, and anti-tryptase immunostaining in order to identify some cellular subpopulations contained in healthy skin biopsies. A nuclear counterstain was made with DAPI. The results in FIG. 3 show that the healthy skin biopsies contain Langerhans cells (CD207), resident T cells (CD3), dendritic cells (HLA-DR), and mast cells (Tryptase) at T0 and after 7 days of culture (T7).

5.2—Cryosection

The analysis can also be carried out on a frozen section in order not to alter the fluorescence of the cells/spheroid(s) upon dehydration.

The culture of the skin biopsy treated according to steps a) and b) of the method of the invention is stopped by fixing the sample for 24 hours in 10 times its volume of 10% formalin. The explant is then rinsed in 10 times its volume of PBS, blotted on absorbent paper, and transferred to an EPPENDORF tube. The EPPENDORF tube is immersed in liquid nitrogen until the explant is frozen.

In the cryostat enclosure, the frozen explant is enclosed at OCT, and then slices of a constant thickness from 3 to 15 μm of the portion of the explant containing the implanted spheroid(s) are made. The slices are placed on slides which are dried for at least a few hours.

A traditional staining with haematoxylin and eosin is performed.

6—Validation of the Model of Inflamed Skin 6.1—Inflammation Markers

The cytokines IL-17A, IL-22, and IFNγ produced by the model were analyzed in the culture media by an ELISA assay using a specific detection kit from Meso Scale Discovery (U-PLEX TH17 Combo 2 Human Reference K15076K) and using a multiplex assay platform (MESO QuickPlex SQ 120).

Figure 4:
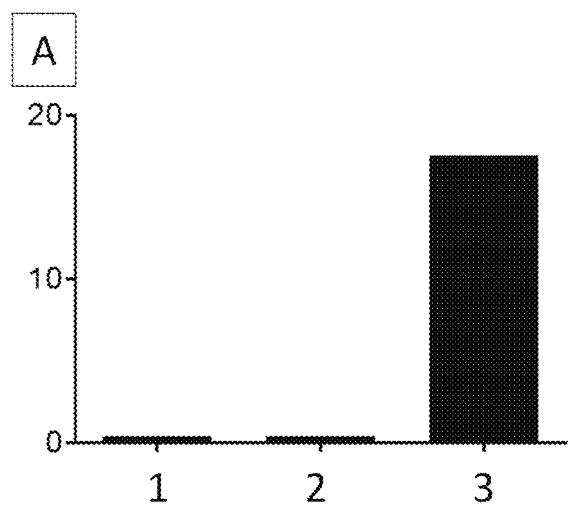
Figure 4:
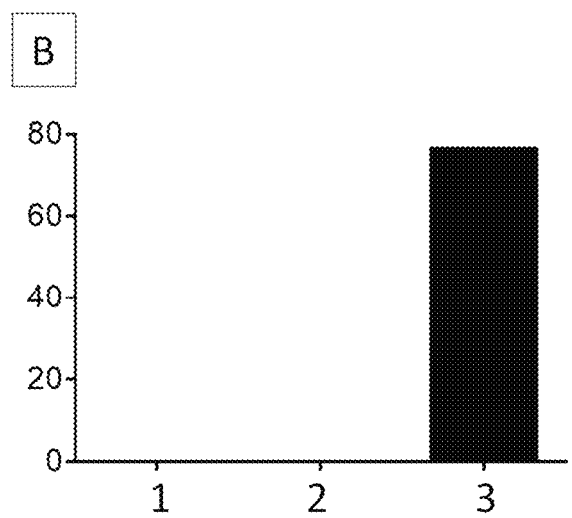

FIG. 4 shows the results obtained in the cytokine assay in different models. NativeSkin® models are skin biopsies that include the epidermis and dermis, and are free of hypodermis. In contrast to the standard NativeSkin® (1) or NativeSkin® models cultured in the presence of the pro Th17/Th1 polarization cocktail (2), the cytokines IL-17A (FIG. 4A) and IL-22 (FIG. 4B) are produced solely by the InflammaSkin® model (3) obtained by the method of the invention.

6.2—Keratinocyte Activation

At the end of step b) of the method of the invention, ex vivo models of inflamed skin show characteristic signs comparable to those observed in the psoriatic lesions of psoriasis patients. The table below illustrates the appearance of some of these markers.

|  | Control biopsy | | | Biopsy treated according to steps a) and b) of the method of the invention | | |
| --- | --- | --- | --- | --- | --- | --- |
|  | T0 | T5 | T7 | T0 | T5 | T7 |
| Apoptosis | − | − | − | − | + | + |
| S100A7 | − | − | − | − | + | ++ |
| KRT16 | − | − | +/− | − | + | +++ |

After 5 days of incubation of the skin biopsy in the presence of the mixture of IL-1β, IL-23, and TGF-β, appearance of the markers S100A7 (psoriasin) and keratin 16 (KRT16), characteristic of keratinocyte hyperproliferation, is observed. The rates of these markers still increase 7 days after polarization of CD4$^+$ T cells activated into Th1/Th17 started.

In addition, apoptosis is observed within the keratinocytes of the epidermis of the ex vivo model of inflamed skin obtained by the method of the invention.

7—Screening for Anti-Inflammatory Compounds

In order to test the relevance of the model of inflamed skin obtained by the method of the invention, compounds known for their anti-inflammatory effect were tested. These are betamethasone di-propionate and the PDE4 inhibitor. Topical applications of these products (constant volume of 10 μL on 8 mm diameter biopsies) were performed immediately after activation and production of the InflammaSkin® model (prophylactic treatment) or after 3 days of culture without treatment (therapeutic treatment) and repeated daily until the 7$^{th}$ day of culture.

Figure 5:
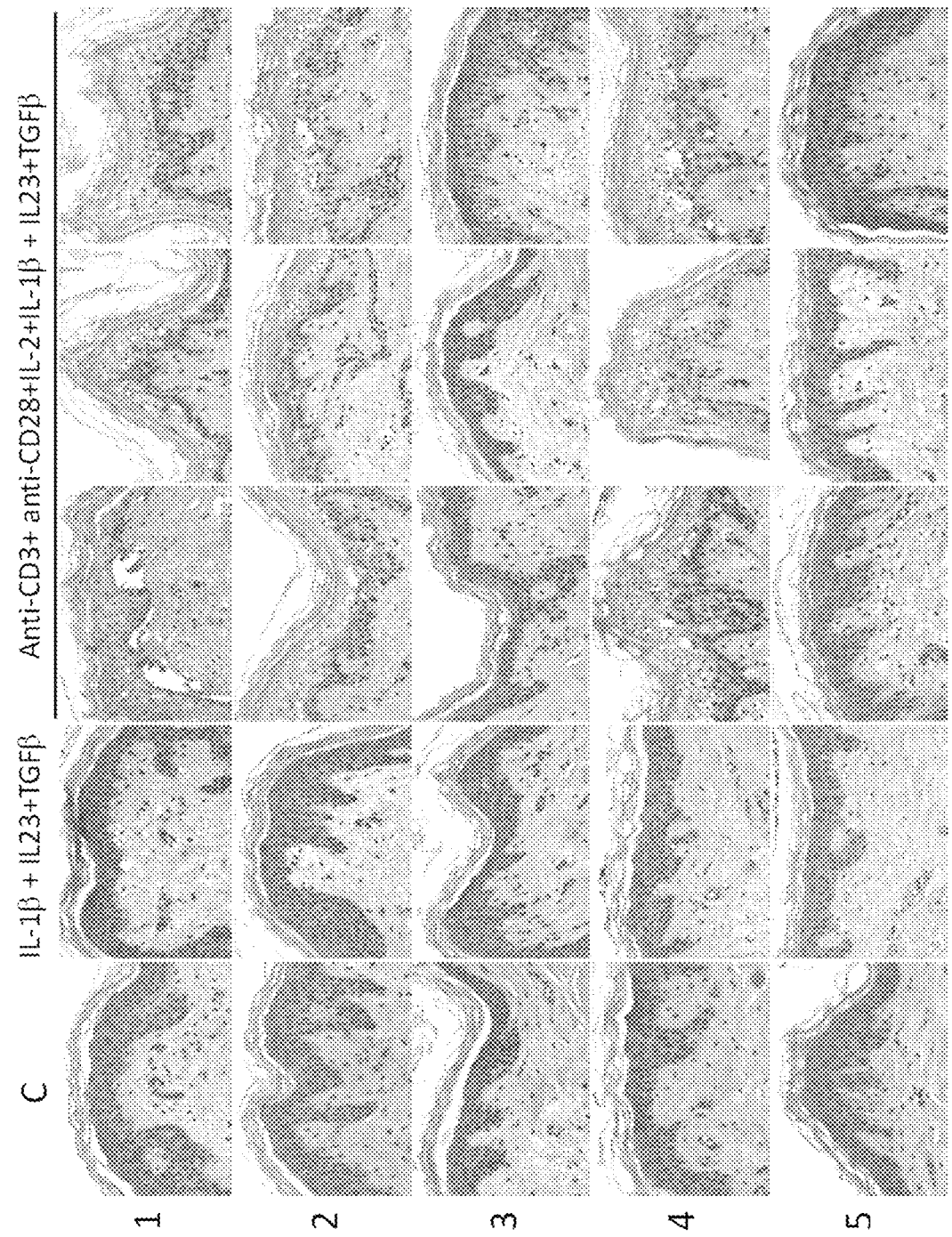
Figure 6:
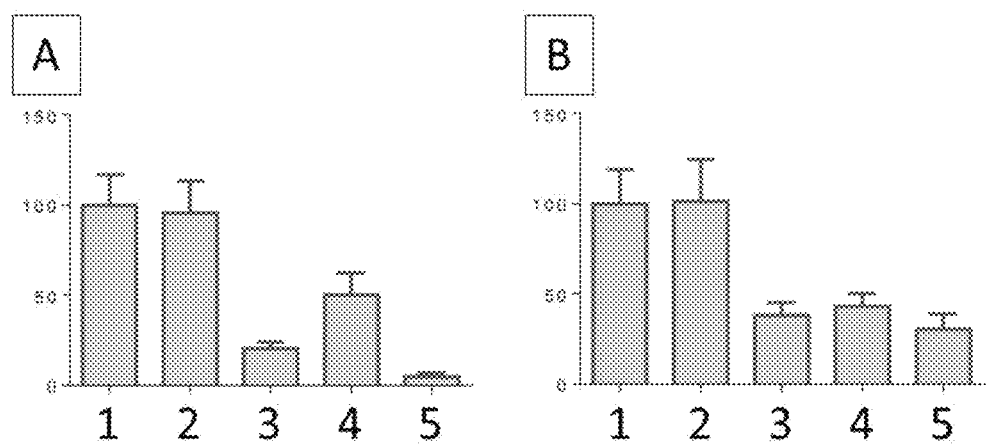
Figure 7:
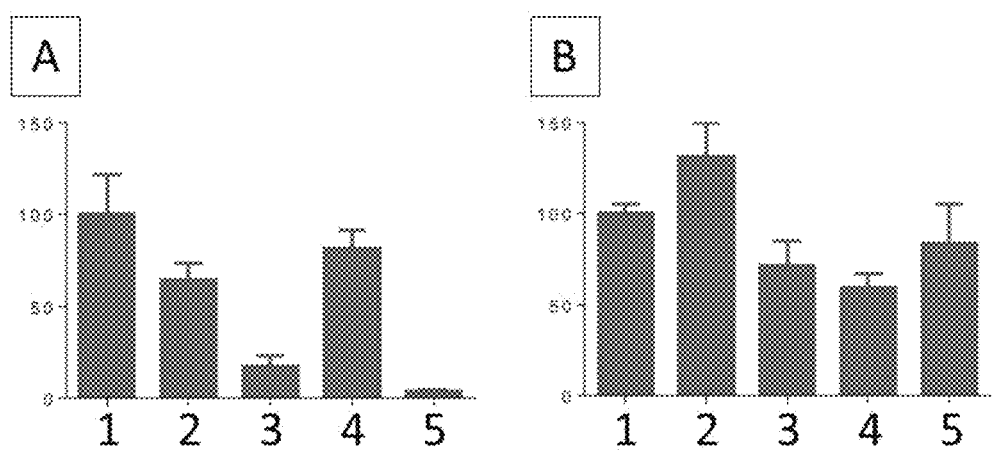
Figure 8:
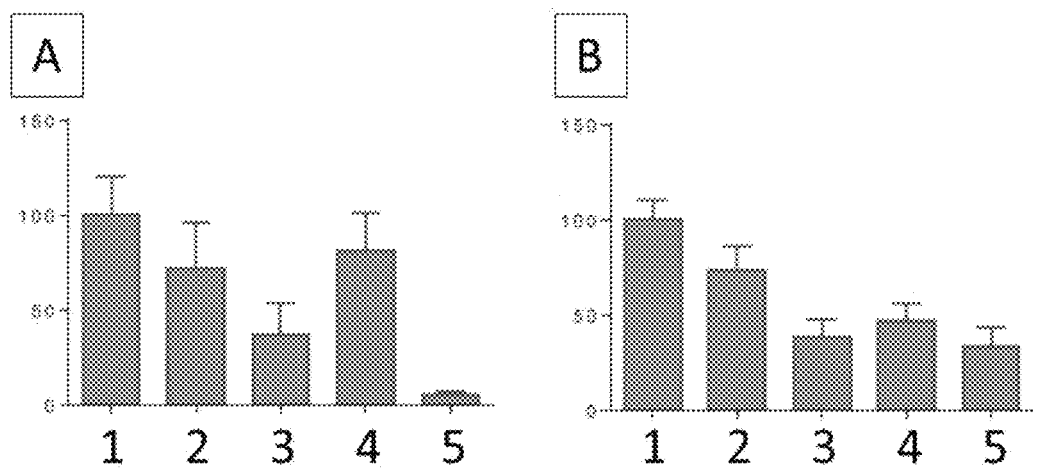

Histological analysis (FIG. 5) shows that the integrity and structure of the skin, particularly the epidermis, and the viability of epidermal cells are preserved during treatment with betamethasone di-propionate and the PDE4 inhibitor as a prophylactic treatment compared to their respective placebo controls.

Figure 9:
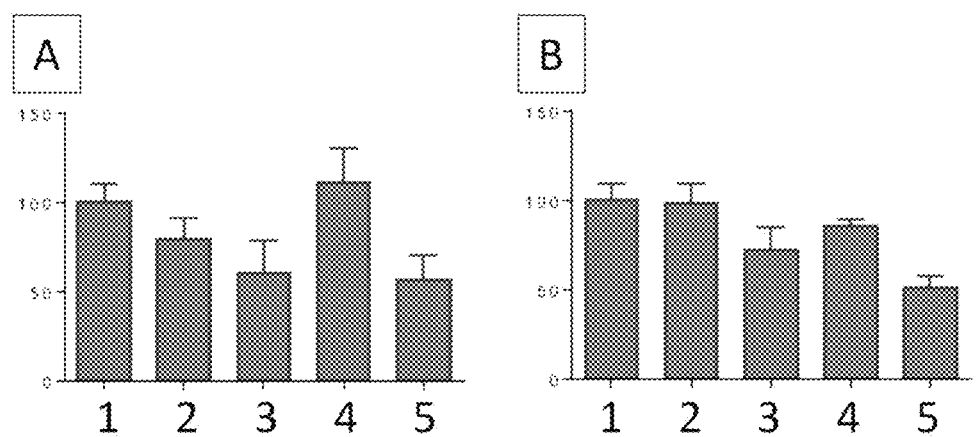
Figure 10:
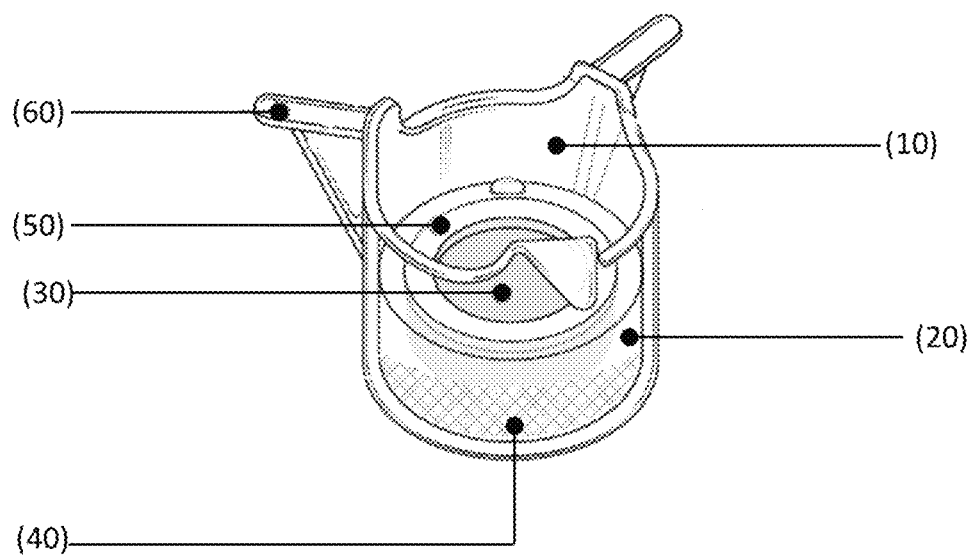

Analysis of the secretion of pro-inflammatory cytokines IL-17A, IL-22, IFNγ, and TNFα (FIGS. 6 to 9) shows that:

IL-17A secretion (FIG. 6) is strongly inhibited by betamethasone di-propionate (3) and the PDE4 inhibitor (5) as a prophylactic treatment compared to their respective placebo controls (FIG. 6A), whereas only betamethasone di-propionate (3) inhibits IL-17A secretion as a therapeutic treatment (FIG. 6B), IL-22 secretion (FIG. 7) is strongly inhibited by betamethasone di-propionate (3) and even more strongly by the PDE4 inhibitor (5) as a prophylactic treatment compared to their respective placebo controls (FIG. 7A), whereas only betamethasone di-propionate (3) inhibits IL-22 secretion as a therapeutic treatment (FIG. 7B), IFNγ secretion (FIG. 8) is strongly inhibited by betamethasone di-propionate (3) and the PDE4 inhibitor (5) as a prophylactic treatment compared to their respective placebo controls (FIG. 8A), whereas only betamethasone di-propionate (3) inhibits IFNγ secretion as a therapeutic treatment (FIG. 8B), TNFα secretion (FIG. 9) is strongly inhibited by betamethasone di-propionate (3) and the PDE4 inhibitor (5) not only as a prophylactic treatment compared to their respective placebo controls (FIG. 9A), but also as a therapeutic treatment (FIG. 9B).

8—Incorporation of the Anti-CD3 Antibody into Dermal Cells

A comparative test relating to the incorporation of an anti-CD3 antibody was carried out on human skin biopsies. 40 ng/μl of anti-CD3e antibody coupled to the fluorochrome Alexa Fluor 647 (ThermoFisher, ref. A51001) were either injected directly into the dermis of a human skin biopsy with a thickness of 4 mm and a diameter of 8 mm, or added to the culture medium in which the skin biopsy is maintained floating. After 24 hours of culture, the skin biopsies are fixed in a 10% formalin solution and embedded in paraffin blocks. Serial sections of a constant thickness of 5 μm of the biopsies are made. The cell nuclei are marked with DAPI. A Leica DM5000 fluorescence microscope is used for analysis.

Figure 11:
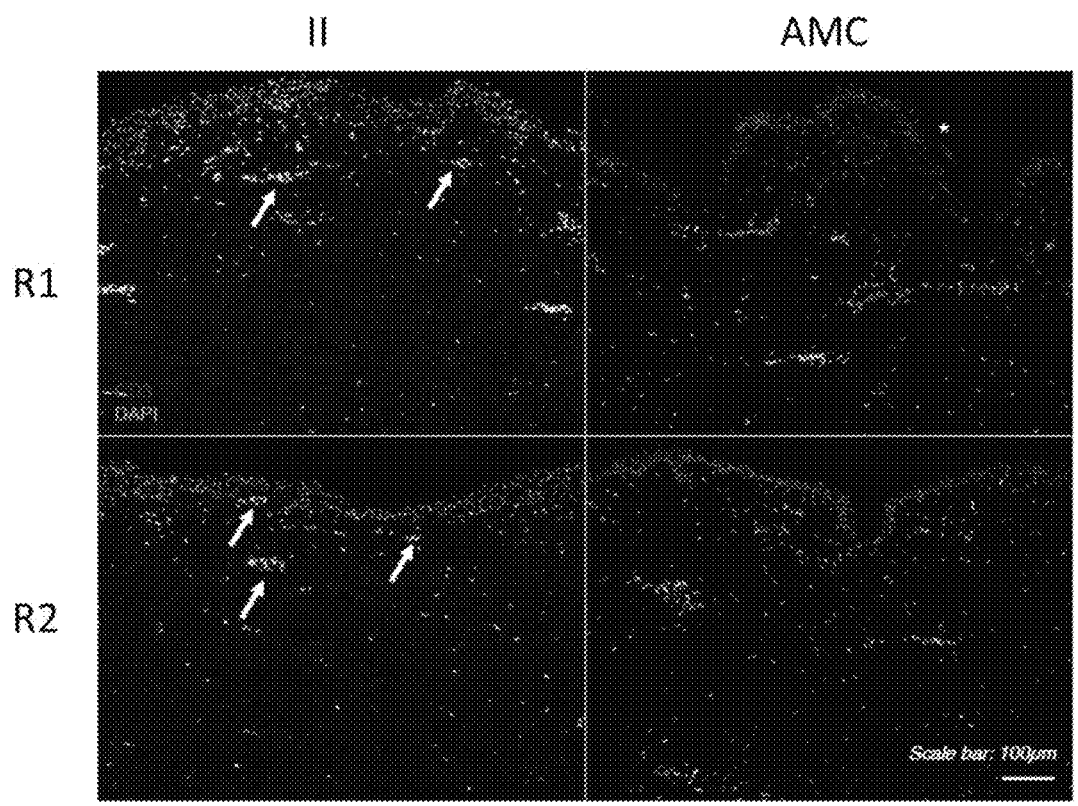
Figure 12:
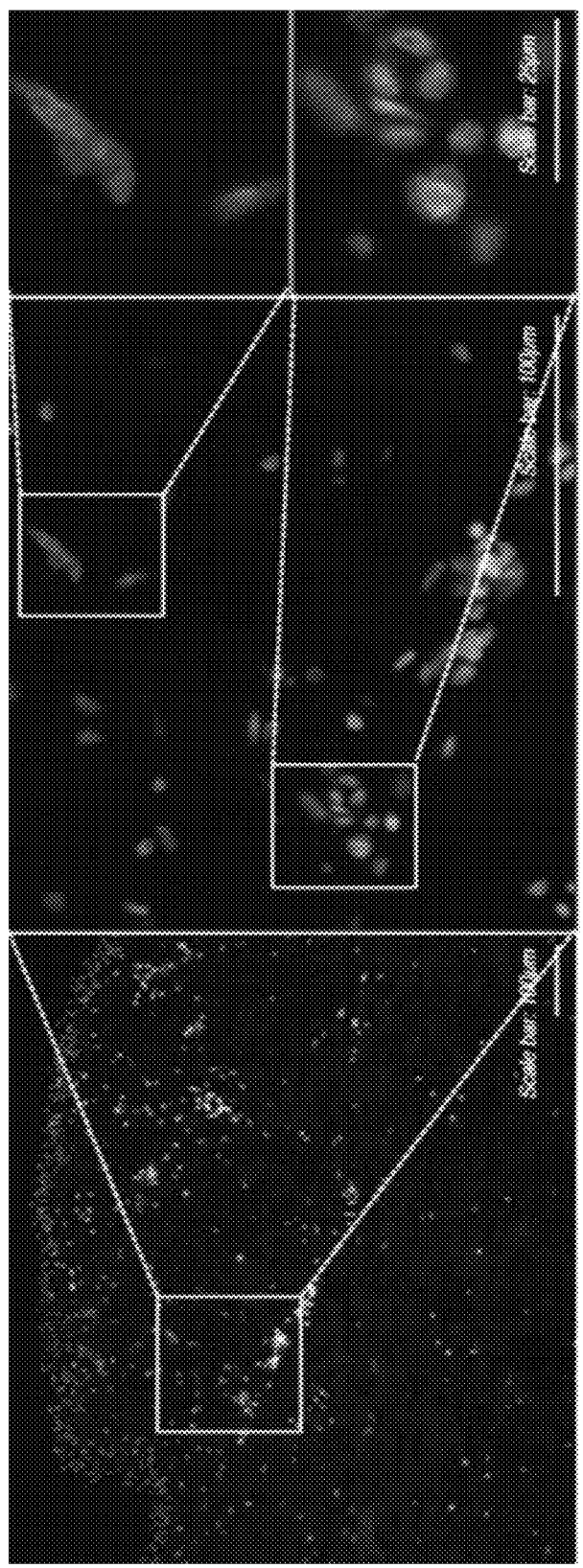
FIG. 12 shows the subcellular location of an anti-CD3 antibody in the dermal cells of a human skin biopsy. The anti-CD3e antibody was injected directly into the dermis of the biopsy.

The incorporation of the anti-CD3e antibody into the dermal cells is materialized by arrows in two separate biopsies (replicates 1 and 2) having undergone an injection of this antibody directly into the dermis (FIG. 11, left panels—II). At high magnification (FIG. 12), it can be seen that the anti-CD3e antibody is incorporated in the cytoplasm of some of the dermal cells.

Conversely, for only one of the two biopsies that have been incubated in a culture medium comprising the anti-CD3e antibody, the detection of this antibody is visible, and materialized by a star, only on the surface of the epidermis (FIG. 11 right panel—AMC/R1). No dermal cells were able to incorporate the anti-CD3e antibody by passive diffusion.

These results show that the anti-CD3 antibody reaches the dermal cells only if it is injected directly into this tissue.

Similar results can be obtained with the anti-CD28 antibody.

9—Screening for Anti-Inflammatory Compounds

In order to test the relevance of the model of inflamed skin obtained by the method of the invention (Hypo-InflammaSkin®), an antibody known for its anti-inflammatory effect was tested. This is the adalimumab anti-TNFα antibody. Biopsies of inflamed skin (Hypo-InflammaSkin®-I) with a thickness of 1 cm were obtained by the method of the invention. A subcutaneous injection (namely into the dermis) of 50 nM adalimumab was performed at T0 (prophylactic treatment, Hypo-InflammaSkin®-I+anti-TNFα-P) or after 3 days of ex vivo culture of the inflamed biopsy (therapeutic treatment, Hypo-InflammaSkin®-I+anti-TNFα-T). After 7 days of ex vivo culture, the culture media are taken, and skin biopsies are fixed in a 10% formalin solution and then embedded in paraffin blocks. Serial sections of a constant thickness of 5 μm of the biopsies are made. The morphological appearance of the skin biopsies is studied under optical microscopy using hematoxylin and eosin staining. The presence of psoriasin (S110A7) is identified by fluorescence microscopy (Leica DM 5000 microscope) using an anti-S100A7 antibody coupled to a fluorochrome. The cell nuclei are marked with DAPI. Biopsies of non-inflamed skin (HypoSkin®-biopsies including the epidermis, dermis, and hypodermis) are used for control.

Figure 13:
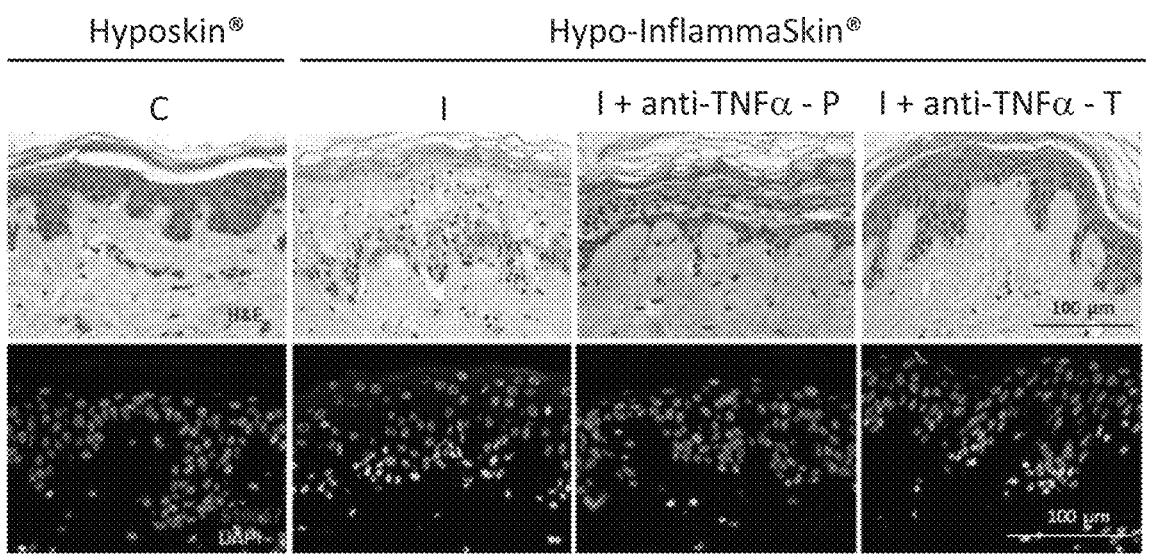
FIG. 13 illustrates the histological characteristics of a skin biopsy that is non-inflamed (C), inflamed according to the method of the invention (I), inflamed and treated by subcutaneous injection of an anti-TNF-α antibody as a prophylactic treatment (I+anti-TNF-α-P), or as a therapeutic treatment (I+anti-TNF-α-T).

Histology analysis (FIG. 13) shows that the integrity and structure of the skin, and more particularly of the epidermis, and the epidermal cell viability are preserved when treated with the anti-TNFα antibody adalimumab as a prophylactic treatment (Hypo-InflammaSkin®-I+anti-TNFα-P) and as a therapeutic treatment (Hypo-InflammaSkin®-I+anti-TNFα-T) compared to a biopsy of inflamed skin not treated with this antibody (Hypo-InflammaSkin®-I).

In addition, psoriasin becomes almost undetectable in samples from an inflamed biopsy treated with anti-TNF-α, thus attesting to the resolution of the inflammation.

Figure 14:
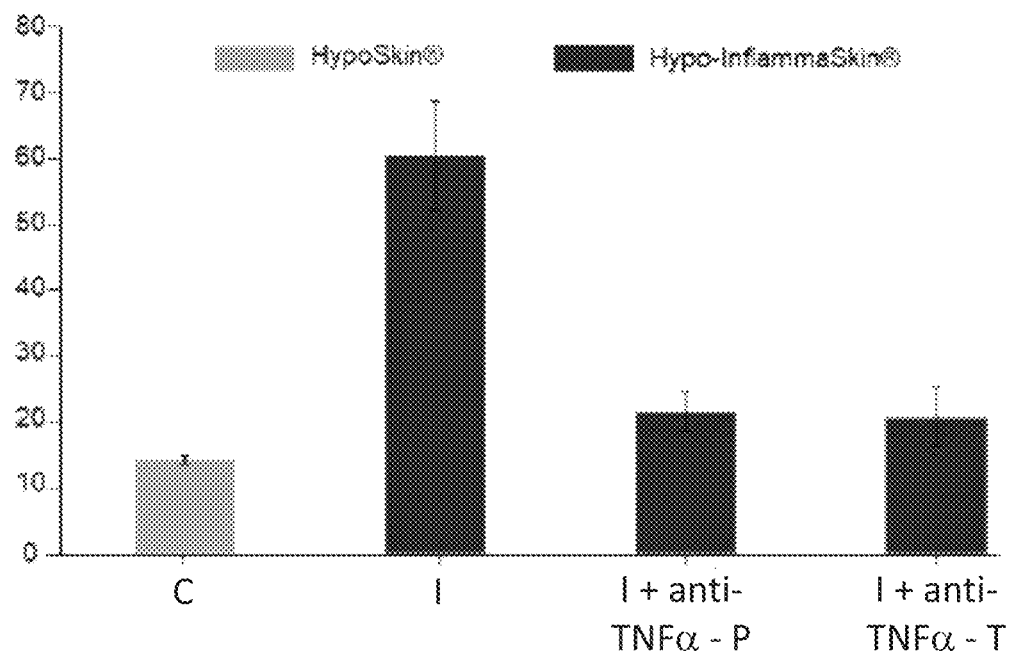
FIG. 14 illustrates the protein synthesis of IL-22 by a skin biopsy that is non-inflamed (C), inflamed according to the method of the invention (I), inflamed according to the method of the invention and treated by subcutaneous injection of an anti-TNF-α antibody as a prophylactic treatment (I+anti-TNF-α-P), or as a therapeutic treatment (I+anti-TNF-α-T). Results are expressed in pg/ml.

Analysis of IL-22 pro-inflammatory cytokine secretion shows that IL-22 secretion (FIG. 14) is strongly inhibited by the anti-TNFα antibody as a prophylactic treatment (Hypo-InflammaSkin®–I+anti-TNFα–P) and as a therapeutic treatment (Hypo-InflammaSkin®–I+anti-TNFα–T) compared to a biopsy of inflamed skin not treated by this antibody (Hypo-InflammaSkin®–I).

These results show that the ex vivo model of inflamed skin obtained by the method of the invention allows screening for anti-inflammatory compounds, and in particular anti-psoriatic compounds, the route of administration of which is a subcutaneous injection.

The invention claimed is:

1. An in vitro method for evaluating the anti-inflammatory efficacy of a compound in an ex vivo model of inflamed skin comprising the following steps:
   a) injecting a first composition, using a hollow needle into the reticular dermis of a healthy mammalian skin biopsy having a thickness of 3 mm to 1 cm, which is a mammalian skin fragment comprising at least the epidermis, the dermis, the epidermal appendages and a portion of the hypodermis, wherein the first composition comprises an effective amount of an anti-CD3 antibody and an anti-CD28 antibody for activating dermal resident T cells, thus allowing homogeneous diffusion of the first composition into all tissues of the biopsy, and activation of the resident T cells of the dermis in the injected mammalian skin biopsy;
   a') depositing the injected mammalian skin biopsy obtained at the end of step a) on a liquid matrix capable of solidifying, said matrix being itself contained in a cell culture insert the bottom of which consists of a porous membrane and said insert being arranged in a container or well, so as to allow, once the matrix has solidified, the 3D integrity of the injected mammalian skin biopsy to be maintained;
   b) incubating the injected mammalian skin biopsy deposited in step a') for at least 3 days in the presence of a second composition comprising an effective amount of a mixture comprising at least IL-1β, IL-23, and TGF-β for obtaining polarization of the T cells activated in step a) into LTh1 polarized T cells and/or LTh17 polarized T cells, and synthesis of inflammation markers, to form the ex vivo model of inflamed skin;
   c) contacting the ex vivo model of inflamed skin with a candidate compound, wherein the ex vivo model of inflamed skin comprises LTh1-polarized T cells and/or LTh17-polarized T cells;
   d) measuring an expression level of at least two inflammation markers of the model of inflamed skin;
   e) comparing the expression level of said at least two inflammation markers obtained in step d) with a control expression level; and
   f) identifying the anti-inflammatory efficacy of said candidate compound when the expression level of said at least two inflammation markers measured in step d) is lower than the control expression level,
   wherein said ex vivo model reflects more precisely and reproducibly the environment of inflamed skin as observed in vivo in a physiological context.

2. The method of claim 1, wherein the injected composition further comprises an effective amount of IL-2.

3. The method according to claim 1, wherein step a) is carried out manually.

4. The method according to claim 1, wherein the incubation step b) lasts at least 5 days.

5. The method according to claim 2, wherein the concentrations in the composition injected in step a) of the method are the following ones:
   between 10 ng/µl and 100 ng/µl for the anti-CD3 and anti-CD28 antibodies, and
   between 1 ng/ml and 20 ng/ml for IL-2.

6. The method according to claim 1, wherein the concentrations in the at least one mixture of the composition used in step b) of the method are the following ones:
   between 1 ng/ml and 50 ng/ml for IL-1β and TGFβ, and
   between 10 ng/ml and 100 ng/ml for IL-23.

7. The method according to claim 1, which also in step d) includes measuring the expression level of at least three inflammation markers selected from the group consisting of IL-8, IL-17A, IL-22, IL-23, IFNγ, TNFα, S100A7, S100A8, S100A9, S100A12, SERPINB3, SERPINB4, SERPINB 13, DEFB4, KRT6A, KRT16, KRT17, CXCL9, CXCL10, CCL18, and CCL20.

8. The method according to claim 1, wherein the healthy skin biopsy previously taken from a mammal used in step a) comprises a dermis, an epidermis, epidermal appendages, and a hypodermis.

9. The method according to claim 2, wherein the concentrations in the composition injected in step (a) of the method are the following ones:
   between 20 ng/µl and 80 ng/µl for the anti-CD3 and anti-CD28 antibodies, and
   from 2 ng/ml to 15 ng/ml for IL-2.

10. The method according to claim 2, wherein the concentrations in the composition injected in step (a) of the method are the following ones:
    30 ng/µl to 70 ng/µl for the anti-CD3 and anti-CD28 antibodies, and
    from 4 ng/ml to 12 ng/ml for IL-2.

11. The method according to claim 1, wherein the concentrations in the at least one mixture of the composition used in step b) of the method are the following ones:
    between 5 ng/ml and 30 ng/ml for IL-1β and TGFβ, and
    from 20 ng/ml to 80 ng/ml for IL-23.

12. The method according to claim 1, wherein the concentrations in the at least one mixture of the composition used in step b) of the method are the following ones:
    from 7 ng/ml to 15 ng/ml for IL-1β and TGFβ, and
    from 30 ng/ml to 60 ng/ml for IL-23.

13. The method according to claim 1, which also in step d) includes measuring the expression level of at least five inflammation markers selected from the group consisting of IL-8, IL-17A, IL-22, IL-23, IFNγ, TNFα, S100A7, S100A8, S100A9, S100A12, SERPINB3, SERPINB4, SERPINB13, DEFB4, KRT6A, KRT16, KRT17, CXCL9, CXCL10, CCL18, and CCL20.

14. The method of claim 1, wherein the composition comprising an effective amount of a mixture comprising at least IL-1β, IL-23, and TGF-β is renewed daily throughout the duration of this step.

15. The method of claim 1, wherein the method is for testing the effectiveness of a compound in preventing inflammation from occurring, and wherein the steps b) and c) are carried out simultaneously.

16. The method of claim 1, wherein the method is for testing the prophylactic efficacy of a compound in preventing inflammation from occurring, and wherein the step c) of, contacting the candidate compound with the skin model takes place prior to steps a) of activating and b) of polarizing the resident T cells in the dermis.

* * * * *